United States Patent
Harder et al.

(10) Patent No.: US 7,341,990 B2
(45) Date of Patent: Mar. 11, 2008

(54) METHODS AND USES OF LEUKOTRIENE $B_4$ HYDROXYLASES TO TREAT DISEASES

(76) Inventors: David R. Harder, W290 S6459 Holiday Rd., Waukesha, WI (US) 53189; James B. Antczak, 5392 S. 48th St., Greenfield, WI (US) 53220; Lane Brostrom, 4381 N. Alpine Ave., Shorewood, WI (US) 53211

( * ) Notice: Subject to any disclaimer, the term of this patent is extended or adjusted under 35 U.S.C. 154(b) by 0 days.

(21) Appl. No.: 11/414,896

(22) Filed: May 1, 2006

(65) Prior Publication Data
US 2006/0247200 A1 Nov. 2, 2006

Related U.S. Application Data

(60) Provisional application No. 60/676,369, filed on Apr. 29, 2005.

(51) Int. Cl.
*A61K 37/00* (2006.01)
*A61K 31/70* (2006.01)
(52) U.S. Cl. .............................. 514/2; 514/45; 514/47
(58) Field of Classification Search ................. 514/45, 514/47; 424/94.1, 94.2; 435/183; 536/26.24
See application file for complete search history.

(56) References Cited

OTHER PUBLICATIONS

Powell, W.S., J. Biological Chemistry, 1984, vol. 259, No. 5, pp. 3082-3089.

Kawashima, H., Archives of Biochemistry and Biophysics, 1997, vol. 347, No. 1, pp. 148-154.

P. M. O'Byrne, Leukotriene B4 Induces Airway Hyperresponsiveness in Dogs, Journal of Applied Physiology, vol. 59, Issue 6 1941-1946, 1985.

Zsuzsanna Csoma, Increase Leukotrienes in Exhaled Condensate in Childhood Asthma, Am J Respir Crit Care Med, vol. 166. pp. 1345-1349, 2002.

*Primary Examiner*—L. E. Crane
(74) *Attorney, Agent, or Firm*—Quarles & Brady LLP

(57) ABSTRACT

Methods and uses are described for treating or preventing diseases of humans or non-human animals by reducing the amount of active leukotriene $B_4$ ($LTB_4$) in those in need of such treatment using $LTB_4$ hydroxylases. In certain embodiments, $LTB_4$ hydroxylase is administered in combination with nicotinamide adenine dinucleotide phosphate and/or an NADPH-cytochrome P-450 reductase. The invention is particularly useful for treating or preventing respiratory diseases that are caused or exacerbated by inflammation.

13 Claims, 3 Drawing Sheets

SEQUENCE LISTING

<160> NUMBER OF SEQ ID NOS: 12

<210> SEQ ID NO 1
<211> LENGTH: 2227
<212> TYPE: DNA
<213> ORGANISM: HOMO SAPIENS

<400> SEQUENCE: 1

```
ggagaggagg ttgtctggga cagactgctc ctgacagaag gatgtcccag ctgagcctgt      60
cctggctggg cctctggcca gtggcagcat ccccttggct gctcctcctg ctggtcgggg     120
cctcctggct cctggcccat gtcctggcct ggacctacgc cttctatgac aactgccgcc     180
gccttcggtg tttcccacaa cccccaagac ggaactggtt ttggggacac cagggcatgg     240
tcaaccccac agaggagggc atgagagttc tgactcagct ggtggccacc tacccccagg     300
gctttaaggt ctggatggga cccatctccc ccctcctcag tttgtgccac cccgacatca     360
tccggtctgt catcaacgcc tcagctgcca ttgcaccaaa ggacaagttc ttctacagct     420
tcctggagcc ctggctgggg gatgggctcc tgctgagtgc tggtgacaag tggagccgcc     480
accgtcggat gctgacgcct gccttccatt tcaacatcct gaagccctat atgaagattt     540
tcaatgagag tgtgaacatc atgcacgcca agtggcagct cctggcctca gagggtagtg     600
cctgtttgga tatgtttgag cacatcagcc tcatgacctt ggacagtcta cagaaatgtg     660
tcttcagctt tgacagccat tgtcaggaga aacccagtga atatattgcc gccatcttgg     720
agctcagtgc ccttgtatca aaagacacc atgagatcct cctgcatatt gacttcctgt      780
attatctcac ccctgatggg cagcgtttcc gcagggcctg ccgcctggtg cacgacttca     840
cagatgccgt catccaggag cggcgccgca ctctccctag ccagggtgtt gatgacttcc     900
tccaagccaa ggccaaatcc aagactttgg acttcattga tgtactcctg ctgagcaagg     960
atgaagacgg gaagaagtta tctgatgagg acataagagc agaagctgac acctttatgt    1020
ttgagggcca tgacaccacg gccagtggtc tctcctgggt cctgtaccac cttgcaaagc    1080
acccagaata ccaggagcgc tgccggcagg aggtgcaaga acttctgaag gaccgtgagc    1140
ctaaagagat tgaatgggac gacctggccc atttgccctt cctgaccatg tgcatgaagg    1200
agagcctgcg gctgcatccc ccagtcccgg tcatctcccg ccatgtcacc aggacattg     1260
tgctcccaga cggccgggtc atccccaaag gcattatctg cctcatcagt gttttcggaa    1320
cccatcacaa cccagctgtg tggccggacc ctgaggtcta cgaccccttt cgctttgacc    1380
cagagaacat caaggagagg tcacctctgg cttttattcc cttctcggca gggcccagga    1440
actgcatcgg gcagacgttc gcgatggcgg agatgaaggt ggtcctggcg ctcacgctgc    1500
tgcgcttccg cgtcctgcct gaccacaccg agccccgcag gaagccggag ctggtcctgc    1560
gcgcagaggg cggactttgg ctgcgggtgg agccctgag ctgagttctg cagagaccca    1620
ctctgacccc actaaaatga cccctgattc atcaaaagtg aagcctagaa ttaccctaag    1680
accctgttcc acagtcctgt attccatcct agatatctac tcaaaataat tgagacaagt    1740
```

```
gttcaaacag aaagacgctt gtgcgtgaat gttcatggcg gccctattca cagtagccaa    1800
acgatgaaaa caaccccaag ctatatatta ccagatgaaa ggataaacaa aatgtggtcc    1860
atccatacaa tggagtatta cacagccata aaaaggaatg aagcagtgat ccctactaca    1920
ctgtggatga agccttgaat gcatgatact gaatgaaaga cgtcagatgc aaaaggtcac    1980
atagtgtact gtgcctttta tacgaaattt ccagaacagg ccaatctgaa gagatgcata    2040
gcggattggt ggctttcagc agctgtgggg aggtgggact gaggagcgac tgctaatcag    2100
tatggggttt cctcccggga tggtgaaaat gttccggacc tagatactga cgaaggtagc    2160
acgacactgt gagtgcacta aatgctattg aattggacac tttgaaatgg tgaatttcgt    2220
ggtatgt                                                              2227
```

```
<210> SEQ ID NO 2
<211> LENGTH: 488
<212> TYPE: PRT
<213> ORGANISM: HOMO SAPIENS

<400> SEQUENCE: 2

Met Ser Gln Leu Ser Leu Ser Trp Leu Gly Leu Trp Pro Val Ala Ala
1               5                   10                  15

Pro Trp Leu Leu Leu Leu Leu Val Gly Ala Ser Trp Leu Leu Ala Val
            20                  25                  30

Leu Ala Trp Thr Tyr Ala Phe Tyr Asp Asn Cys Arg Arg Leu Cys Phe
        35                  40                  45

Pro Gln Pro Pro Arg Arg Asn Trp Phe Trp Gly His Gln Met Val Asn
    50                  55                  60

Pro Thr Glu Glu Gly Met Arg Val Leu Thr Gln Leu Ala Thr Tyr Pro
65                  70                  75                  80

Gln Gly Phe Lys Val Trp Met Gly Pro Ile Ser Leu Ser Leu Cys
                85                  90                  95

His Pro Asp Ile Ile Arg Ser Val Ile Asn Ser Ala Ala Ile Ala Pro
            100                 105                 110

Lys Asp Lys Phe Phe Tyr Ser Phe Leu Pro Trp Leu Gly Asp Gly Leu
        115                 120                 125

Leu Leu Ser Ala Gly Asp Lys Trp Arg His Arg Arg Met Leu Thr Pro
130                 135                 140

Ala Phe His Phe Asn Ile Leu Pro Tyr Met Lys Ile Phe Asn Glu Ser
145                 150                 155                 160

Val Asn Ile Met His Ala Trp Gln Leu Leu Ala Ser Glu Gly Ser Ala
                165                 170                 175

Cys Leu Asp Met Phe His Ile Ser Leu Met Thr Leu Asp Ser Leu Gln
            180                 185                 190

Lys Cys Val Phe Phe Asp Ser His Cys Gln Glu Lys Pro Ser Glu Tyr
        195                 200                 205

Ile Ala Ala Leu Glu Leu Ser Ala Leu Val Ser Lys Arg His His Glu
    210                 215                 220

Ile Leu His Ile Asp Phe Leu Tyr Tyr Leu Thr Pro Asp Gly Gln Arg
225                 230                 235                 240

Phe Arg Ala Cys Arg Leu Val His Asp Phe Thr Asp Ala Val Ile Gln
                245                 250                 255

Arg Arg Arg Thr Leu Pro Ser Gln Gly Val Asp Asp Phe Leu Gln Lys
            260                 265                 270

Ala Lys Ser Lys Thr Leu Asp Phe Ile Asp Val Leu Leu Leu Lys Asp
        275                 280                 285
```

```
Glu Asp Gly Lys Lys Leu Ser Asp Glu Asp Ile Arg Ala Ala Asp Thr
            290                 295                 300
Phe Met Phe Glu Gly His Asp Thr Thr Ala Ser Gly Ser Trp Val Leu
305                 310                 315                 320
Tyr His Leu Ala Lys His Pro Glu Tyr Gln Glu Cys Arg Gln Glu Val
                325                 330                 335
Gln Glu Leu Leu Lys Asp Arg Glu Pro Lys Ile Glu Trp Asp Asp Leu
            340                 345                 350
Ala His Leu Pro Phe Leu Thr Met Cys Lys Glu Ser Leu Arg Leu His
            355                 360                 365
Pro Pro Val Pro Val Ile Ser Arg Val Thr Gln Asp Ile Val Leu Pro
        370                 375                 380
Asp Gly Arg Val Ile Pro Lys Ile Ile Cys Leu Ile Ser Val Phe Gly
385                 390                 395                 400
Thr His His Asn Pro Ala Trp Pro Asp Pro Glu Val Tyr Asp Pro Phe
                405                 410                 415
Arg Phe Asp Pro Glu Ile Lys Glu Arg Ser Pro Leu Ala Phe Ile Pro
            420                 425                 430
Phe Ser Ala Gly Arg Asn Cys Ile Gly Gln Thr Phe Ala Met Ala Glu
            435                 440                 445
Met Lys Val Leu Ala Leu Thr Leu Leu Arg Phe Arg Val Leu Pro Asp
        450                 455                 460
His Thr Pro Arg Arg Lys Pro Glu Leu Val Leu Arg Ala Glu Gly Gly
465                 470                 475                 480
Leu Leu Arg Val Glu Pro Leu Ser
                485

<210> SEQ ID NO 3
<211> LENGTH: 5050
<212> TYPE: DNA
<213> ORGANISM: HOMO SAPIENS

<400> SEQUENCE: 3
agaagaaggg gagaggaggt tgtgtgggac aaggtgctcc tgacagaagg atgccacagc      60
tgagcctgtc ctcgctgggc cttttggccaa tggcagcatc ccgtggctg ctcctgctgc     120 tggttggggc ctcctggctc ctggcccgca tcctggcctg acctatacc ttctatgaca     180 actgctgccg cctccggtgt ttcccgcaac ccccgaaacg gaattggttc ttgggtcacc     240
tgggcctgat tcacagctcg gaggaaggtc tcctatacac acaaagcctg gcatgcacct     300
tcggtgatat gtgctgctgg tgggtggggc cctggcacgc aatcgtccgc atcttccacc     360
ccacctacat caagcctgtg ctctttgctc cagctgccat tgtaccaaag acaaggtct     420 tctacagctt cctgaagccc tggctggggg atgggctcct gctgagtgct ggtgaaaagt     480
ggagccgcca ccgtcggatg ctgacgcctg ccttccattt caacatcctg aagcccatata    540 tgaagatttt caatgagagt gtgaacatca tgcatgccaa gtggcagctc ctggcctcag     600
agggtagtgc ccgtctggac atgtttgagc acatcagcct catgaccttg gacagtctgc     660
agaaatgtgt cttcagcttt gacagccatt gccaggagaa gcccagtgaa tatattgccg     720
ccatcttgga gctcagtgcc cttgtgacaa aaagacacca gcagatcctc ctgtacatag     780
acttcctgta ttatctcacc cctgatgggc agcgtttccg cagggcctgc gcctggtgc      840 acgacttcac agatgacgtc atccaggagc ggcgccgcac cctccctagc cagggtgttg     900
atgacttcct ccaagccaag gccaaatcca agactttgga cttcattgat gtactcctgc     960
```

```
tgagcaagga tgaagatggg aagaagttgt ccgatgagga cataagagca gaagctgaca    1020
cctttatgtt tgagggccat gacaccacag ccagtggtct ctcctgggtc ctgtaccacc    1080
ttgcaaagca cccggaatac caggagcgct gtcggcagga ggtacaagag cttctgaagg    1140
accgtgagcc taaagagatt gaatgggacg acctggccca gctgcccttc ctgaccatgt    1200
gcattaagga gagcctgagg ctgcatcccc cagtccctgc cgtctctcgc tgctgcaccc    1260
aagacattgt gctcccagac ggccgggtca tccccaaagg cattatctgc ctcatcagtg    1320
tttttggaac ccatcacaac ccagccgtgt ggccggaccc tgaggtctat gaccccttc     1380 gctttgaccc aaagaacatc aaggagaggt cacctctggc ttttattccc ttctcagcag    1440
ggcccaggaa ctgcatcggg caggcgttcg cgatggcgga gatgaaggtg gtcctggggc    1500
tcacgctgct ggccttccgc gtcctgcctg accacaccga gccccgcagg aagccggagc    1560
tggtcctgcg cgcagagggc ggactttggc tgcgggtgga gccctgagc tgagttctgc     1620 agagacccac tctgacccca ctaaaatgac ccctgattca tcaaaagtga ggcctagaat    1680
taccctaaga ccctgttcca cagtcctgta ttccatccta gatatctact caaaataatt    1740
gagacaagtg ttcaaacaga aagacgcttg tgcggaatgt tcatggcagc cctattcaca    1800
gtagcccaaa cgatgaaaac accccaagct atatattacc agataaaagg ataaacacaa    1860
tatggtccat ccatacactg gagtattaca cagccataaa aaggaatgaa gcagtgatcc    1920
ccactacact gtggatgaac cttgaatgca tgatactgaa tgaaagacat cagatgcaaa    1980
aggtcacata gtgtactgtc cttttatatg gaaatttcca gaacaggcca atctgaagag    2040
atgtatagtg gattggtggc tttcagcagc tgtggggagg tgggactgag gagcgactgc    2100
taatcaggat ggggttttct cctgggatgg tgaaaatgtt ccggacctag atagtgatga    2160
aggtagcacg acactgtgag tgcactaaat gctattgaat tagacactt agaatggttg      2220 aaatagtgat tttctatgtga attctaccta aacatgctat tacagctcat atatacttt    2280 tccatctgga ttcttcacaa aagaatatgt tgtgagcatc tttccatgat attaaatcat    2340
cttaggaaac attattttgt gttcttcaaa atgtgcatgt taagtattca aatcagtctt    2400
aaatttttaa aaatatgtaa tttagaaaaa taatttaaaa ggttttgttt cagtttgtaa    2460
gatttctttt ctggcacttt aatggcttga ggtatcatta tcagttacaa attgagttat    2520
tcttcatcaa atgactttg gagtagagat tttatttta tagcaataga tgcacagata      2580
ttcctgtaag atacaggtgt ggttagacac ttttctagaa caggcatgcc ctgcaaactc    2640
cacagacact gactgttttt gtcctatgaa caagcagacc actgagaagg gagaaggtga    2700
cattttagct ttcccaggta aaagtggttt tcatcctcac accaatttta tggactggac    2760
gttaactctc ttgctcaagg tcactctgtg agtggaagag tggggataaa tctggttcgt    2820
ttggcatcag aggccatgac ttttcctacc acagaagtaa ttttcaaagt aagtctctgc    2880
cctaggcaca tcagatcacc tggggaccac tccagagtga gtagacaaga ctttgacagg    2940
ggtgcctaat tttttttttt ttttttgaga tggagtctcg ctctgttgcc caggctggag    3000
tgcggtggca tgatctcggt tcattgcaac ctccgcctcc tgcgttcggg tgattgacct    3060
gtctcggcct cccgggtggc tgggattgca ggcacccacc accacgtcca gctaattgtt    3120 gtattttga tagaggcggg gtttcgccat gttacactgg ctggtgttga actcctaacc      3180
tcaggtgatc cacctgcctc ggcctcccaa agtgctggga ttacaggcct ggccccagtt    3240
tgatagtttg ttatcatgtt atacgtacac ttagaataat gatccagcca tctcattcta    3300
```

```
acagcaatga gaacttaggc tccctctct actaaagtac aaaagttagc tggtcgtggt    3360
ggtgcgggcc tgtggtccca gctgctcggg aggttgatgc aggagaatca cttgaaaccc    3420
acaggcggag gttgcggtgg gctggggtgg tgccactgcg ctccagcctg ggggaggggg    3480
acatagcgag actcggtctc aaaaacaaaa caaaacaaaa caaaacaaaa caaaacaaaa    3540
caaaacaaaa cactgccaaa ctgttttcca agcatctgca tcgtgtttaa tttccataag    3600
taacgtatga gaattctagg tcctccaaat aattagcagt ccttcgtagg gtcagttttt    3660
gtttcagcct tccttatggg tatgctgtgg catatccctg agattttaat tcgcattttc    3720
cagtgactaa gggtgttgaa ccactcgtgc cttcctgtgc ctatttgaca ctcctatatt    3780
ttctttggag aagagtctgt tcaatcatct gctcattaaa ttttccttcg attgtttgcc    3840
ttcttattgt tggattttga gagttctatg tacaagtcct tgtcagtcg tgtgatttgc    3900 aagtcttctt cctagactct gaagtttctt tctttcatag agcaaatgtt ttaaattttt    3960
atgaggtaag acttctcagc attattttg gtgaattatg tttatactgc catatatagg    4020
aactctttgc ttaactggag gtcatggaga ttttctccta catttctctt taaaagtttt    4080
atagtttcag agtttacatg taattccata atctccattt agttaaattt tgtgtggggt    4140
gtgaactgtg gtttaactgt tttcttgtat atggatatcc aattgtttca cacaattttt    4200
ttgaaaagaa tatccttggc agggcacggt agctcacacc tgtaatccca gcactttagg    4260
aggtcaaggt gggcagatca tgaggtcagg agtttgagac cagcctggcc aatatggtga    4320
aaccacgtct ctattaaaaa tagaaaaatt agccaggcgt ggtggtgtgt gcctgtattc    4380
acagctgctt ggatggctga ggcaggagaa tcgcttgaac ccaggagtca gaggtttcag    4440
tgagccgaga ttgtgccact gcactccagc ctgggtgaaa gagctagatt ctctctctca    4500
aaaaaaaaaa aaaaaggaa agaaagaaag aaaagaaaag aaaatcccctt tttgctttaa    4560 cttgcccttg caggttttgta gaaactcaat tgttgaaatt tgggtggata aatttctgga    4620
ttttctatct attccatgtt ggaccaatac cacactgccc tagtcactgt tgcattatag    4680
tatatcttta aaggagtaat gggaatcctt caactacatt ttttccccca ataattttg    4740 gctattctgc ttcttttgtg tttctatgta aattttatca tcagtgtgtc tatttctaca    4800
aatagtcctg atagggtttg aattgggatt tctgtgaatc tatagatcaa tctgaggaga    4860
cttaataatg atattgattc tcccaattca tgaatatagt ataccctgt atttatttgt    4920 tttcttgaat ttctttatc attgtttgt agttttcacc atgacagtct tgcacatatt    4980
ttgttaaatg tacagctgag aattaattt tttctggtgt acaatgctaa taaaatggtg    5040
actttaaaag                                                         5050
```

<210> SEQ ID NO 4
<211> LENGTH: 488
<212> TYPE: PRT
<213> ORGANISM: HOMO SAPIENS

<400> SEQUENCE: 4

```
Met Pro Gln Leu Ser Leu Ser Ser Leu Gly Leu Trp Pro Met Ala Ala
 1               5                  10                  15

Pro Trp Leu Leu Leu Leu Leu Val Gly Ala Ser Trp Leu Leu Ala Ile
            20                  25                  30

Leu Ala Trp Thr Tyr Thr Phe Tyr Asp Asn Cys Cys Arg Leu Cys Phe
        35                  40                  45

Pro Gln Pro Pro Lys Arg Asn Trp Phe Leu Gly His Leu Leu Ile His
    50                  55                  60
```

-continued

```
Ser Ser Glu Glu Gly Leu Leu Tyr Thr Gln Ser Leu Cys Thr Phe Gly
65              70                  75                  80

Asp Met Cys Cys Trp Val Gly Pro Trp His Ile Val Arg Ile Phe
                85                  90                  95

His Pro Thr Tyr Ile Lys Pro Val Leu Phe Pro Ala Ala Ile Val Pro
            100                 105                 110

Lys Asp Lys Val Phe Tyr Ser Phe Leu Pro Trp Leu Gly Asp Gly Leu
            115                 120                 125

Leu Leu Ser Ala Gly Glu Lys Trp Arg His Arg Met Leu Thr Pro
    130                 135                 140

Ala Phe His Phe Asn Ile Leu Pro Tyr Met Lys Ile Phe Asn Glu Ser
145                 150                 155                 160

Val Asn Ile Met His Ala Trp Gln Leu Leu Ala Ser Glu Gly Ser Ala
                165                 170                 175

Arg Leu Asp Met Phe His Ile Ser Leu Met Thr Leu Asp Ser Leu Gln
            180                 185                 190

Lys Cys Val Phe Phe Asp Ser His Cys Gln Glu Lys Pro Ser Glu Tyr
    195                 200                 205

Ile Ala Ala Leu Glu Leu Ser Ala Leu Val Thr Lys Arg His Gln Gln
    210                 215                 220

Ile Leu Tyr Ile Asp Phe Leu Tyr Tyr Leu Thr Pro Asp Gly Gln Arg
225                 230                 235                 240

Phe Arg Ala Cys Arg Leu Val His Asp Phe Thr Asp Ala Val Ile Gln
                245                 250                 255

Arg Arg Arg Thr Leu Pro Ser Gln Gly Val Asp Asp Phe Leu Gln Lys
            260                 265                 270

Ala Lys Ser Lys Thr Leu Asp Phe Ile Asp Val Leu Leu Leu Lys Asp
        275                 280                 285

Glu Asp Gly Lys Lys Leu Ser Asp Glu Asp Ile Arg Ala Ala Asp Thr
290                 295                 300

Phe Met Phe Glu Gly His Asp Thr Thr Ala Ser Gly Ser Trp Val Leu
305                 310                 315                 320

Tyr His Leu Ala Lys His Pro Glu Tyr Gln Glu Cys Arg Gln Glu Val
                325                 330                 335

Gln Glu Leu Leu Lys Asp Arg Glu Pro Lys Ile Glu Trp Asp Asp Leu
            340                 345                 350

Ala Gln Leu Pro Phe Leu Thr Met Cys Lys Glu Ser Leu Arg Leu His
        355                 360                 365

Pro Pro Val Pro Ala Val Ser Arg Cys Thr Gln Asp Ile Val Leu Pro
370                 375                 380

Asp Gly Arg Val Ile Pro Lys Ile Ile Cys Leu Ile Ser Val Phe Gly
385                 390                 395                 400

Thr His His Asn Pro Ala Trp Pro Asp Pro Glu Val Tyr Asp Pro Phe
                405                 410                 415

Arg Phe Asp Pro Lys Ile Lys Glu Arg Ser Pro Leu Ala Phe Ile Pro
            420                 425                 430

Phe Ser Ala Gly Arg Asn Cys Ile Gly Gln Ala Phe Ala Met Ala Glu
        435                 440                 445

Met Lys Val Leu Gly Leu Thr Leu Leu Arg Phe Arg Val Leu Pro Asp
    450                 455                 460

His Thr Pro Arg Arg Lys Pro Glu Leu Val Leu Arg Ala Glu Gly Gly
465                 470                 475                 480
```

```
Leu Leu Arg Val Glu Pro Leu Ser
            485
```

<210> SEQ ID NO 5
<211> LENGTH: 1980
<212> TYPE: DNA
<213> ORGANISM: HOMO SAPIENS

<400> SEQUENCE: 5

| | | |
|---|---|---|
| accctcactc accacccatc tgccctgcag gatgccacag ctgagcctgt cctcgctggg | 60 |
| cctttggcca atggcagcat ccccgtggct gctcctgctg ctggttgggg cctcctggct | 120 |
| cctggcccgc atcctggcct ggacctatac cttctatgac aactgctgcc gcctccggtg | 180 |
| tttcccgcaa cccccgaaac ggaattggtt cttgggtcac ctgggcctgg tcaccccac | 240 |
| ggagcagggc atgagggtcc tgactcagct ggtggccacc taccccagg gctttaaggt | 300 |
| ctggatgggc cccatcttcc ccgtcatccg ttttgccac cccaacatca tccggtctgt | 360 |
| catcaacgcc tcagctgcca ttgtaccaaa ggacaaggtc ttctacagct tcctgaagcc | 420 |
| ctggctgggg gatgggctcc tgctgagtgc tggtgaaaag tggagccgcc accgtcggat | 480 |
| gctgacgcct gccttccatt tcaacatcct gaagccctat atgaagattt tcaatgagag | 540 |
| tgtgaacatc atgcatgcca gtggcaact cctggcctca aaagggtatg cccgtctgga | 600 |
| catgtttgag cacatcagcc tcatgacctt ggacagtctg cagaaatgtg tcttcagctt | 660 |
| tgacagccat tgccaggaga agcccagtga atatattgcc gccatcttgg agctcagtgc | 720 |
| ccttgtgaca aaaagacacc agcagatcct cctgtacata gacttcctgt attatctcac | 780 |
| ccctgatggg cagcgtttcc gcagggcctg ccgcctggtg cacgacttca cagatgccgt | 840 |
| catccaggag cggcgccgca ccctccctag ccagggtgtt gatgacttcc tccaagccaa | 900 |
| ggccaaatcc aagactttgg acttcattga tgtactcctg ctgagcaagg atgaagatgg | 960 |
| gaagaagttg tccgatgagg acataagagc agaagctgac acctttatgt ttgagggcca | 1020 |
| tgacaccaca gccagtggtc tctcttgggt cctgtaccac cttgcaaagc acccagaata | 1080 |
| ccaggagcgc tgtcggcagg aggtgcaaga gcttctgaag gaccgtgagc ctaaagagat | 1140 |
| tgaatgggac gacctggccc agctgcccett cctgaccatg tgcattaagg agagcctgag | 1200 |
| gctgcatccc ccagtccctg ccgtctctcg ctgctgcacc caagacattg tgctcccaga | 1260 |
| cggccgggtc atccccaaag gcattatctg cctcatcagt gttttttggaa cccatcacaa | 1320 |
| cccgccgtg tggccggacc ctgaggtcta tgaccccttt cgctttgacc caagaaacat | 1380 |
| caaggagagg tcacctctgg ctttttattcc cttctcagca gggcccagga actgcatcgg | 1440 |
| gcaggcgttc gcgatggcgg agatgaaggt ggtcctgggg ctcacgctgc tgcgcttccg | 1500 |
| cgtcctgcct gaccacaccg agccccgcag gaagccggag ctggtcctgc gcgcagaggg | 1560 |
| cggaatttgg ctgcgggtgg agccctgag ctgagttctg cagagaccca ctctgacccc | 1620 |
| actaaaatga cccctgattc atcaaaagtg aggcctagaa ttaccctaag accctgttcc | 1680 |
| acagtcctgt attctatcct agatatctac tcaaaataat tgagacaagt gttcaaacag | 1740 |
| aaagacgctt gtgcgtgaat gttcatggca gccctattca cagtagccaa acgatgaaaa | 1800 |
| caaccccaag ctatatatta ccagatgaaa ggataaacaa aatatggtcc atccatacaa | 1860 |
| tggagtatta cacagccata aaaggaatg aagcagtgat ccccactaca ctgtggatga | 1920 |
| accttgaatg catgatactg aatgaaagac atcagatgca aaaggtcaca tagtgtactg | 1980 |

<210> SEQ ID NO 6

<211> LENGTH: 488
<212> TYPE: PRT
<213> ORGANISM: HOMO SAPIENS

<400> SEQUENCE: 6

```
Met Pro Gln Leu Ser Leu Ser Leu Gly Leu Trp Pro Met Ala Ala
1               5                   10                  15

Pro Trp Leu Leu Leu Leu Val Gly Ala Ser Trp Leu Leu Ala Ile
            20                  25                  30

Leu Ala Trp Thr Tyr Thr Phe Tyr Asp Asn Cys Cys Arg Leu Cys Phe
            35                  40                  45

Pro Gln Pro Pro Lys Arg Asn Trp Phe Leu Gly His Leu Leu Val Thr
50                  55                  60

Pro Thr Glu Gln Gly Met Arg Val Leu Thr Gln Leu Ala Thr Tyr Pro
65                  70                  75                  80

Gln Gly Phe Lys Val Trp Met Gly Pro Ile Phe Val Ile Arg Phe Cys
                85                  90                  95

His Pro Asn Ile Ile Arg Ser Val Ile Asn Ser Ala Ala Ile Val Pro
            100                 105                 110

Lys Asp Lys Val Phe Tyr Ser Phe Leu Pro Trp Leu Gly Asp Gly Leu
        115                 120                 125

Leu Leu Ser Ala Gly Glu Lys Trp Arg His Arg Arg Met Leu Thr Pro
130                 135                 140

Ala Phe His Phe Asn Ile Leu Pro Tyr Met Lys Ile Phe Asn Glu Ser
145                 150                 155                 160

Val Asn Ile Met His Ala Trp Gln Leu Leu Ala Ser Lys Gly Tyr Ala
                165                 170                 175

Arg Leu Asp Met Phe His Ile Ser Leu Met Thr Leu Asp Ser Leu Gln
            180                 185                 190

Lys Cys Val Phe Phe Asp Ser His Cys Gln Glu Lys Pro Ser Glu Tyr
        195                 200                 205

Ile Ala Ala Leu Glu Leu Ser Ala Leu Val Thr Lys Arg His Gln Gln
210                 215                 220

Ile Leu Tyr Ile Asp Phe Leu Tyr Tyr Leu Thr Pro Asp Gly Gln Arg
225                 230                 235                 240

Phe Arg Ala Cys Arg Leu Val His Asp Phe Thr Asp Ala Val Ile Gln
                245                 250                 255

Arg Arg Arg Thr Leu Pro Ser Gln Gly Val Asp Asp Phe Leu Gln Lys
            260                 265                 270

Ala Lys Ser Lys Thr Leu Asp Phe Ile Asp Val Leu Leu Leu Lys Asp
        275                 280                 285

Glu Asp Gly Lys Lys Leu Ser Asp Glu Asp Ile Arg Ala Ala Asp Thr
290                 295                 300

Phe Met Phe Glu Gly His Asp Thr Thr Ala Ser Gly Ser Trp Val Leu
305                 310                 315                 320

Tyr His Leu Ala Lys His Pro Glu Tyr Gln Glu Cys Arg Gln Glu Val
                325                 330                 335

Gln Glu Leu Leu Lys Asp Arg Glu Pro Lys Ile Glu Trp Asp Asp Leu
            340                 345                 350

Ala Gln Leu Pro Phe Leu Thr Met Cys Lys Glu Ser Leu Arg Leu His
        355                 360                 365

Pro Pro Val Pro Ala Val Ser Arg Cys Thr Gln Asp Ile Val Leu Pro
370                 375                 380

Asp Gly Arg Val Ile Pro Lys Ile Ile Cys Leu Ile Ser Val Phe Gly
```

```
                385                 390                 395                 400
Thr His His Asn Pro Ala Trp Pro Asp Pro Glu Val Tyr Asp Pro Phe
                405                 410                 415
Arg Phe Asp Pro Lys Ile Lys Glu Arg Ser Pro Leu Ala Phe Ile Pro
                420                 425                 430
Phe Ser Ala Gly Arg Asn Cys Ile Gly Gln Ala Phe Ala Met Ala Glu
                435                 440                 445
Met Lys Val Leu Gly Leu Thr Leu Leu Arg Phe Arg Val Leu Pro Asp
        450                 455                 460
His Thr Pro Arg Arg Lys Pro Glu Leu Val Leu Arg Ala Glu Gly Gly
465                 470                 475                 480
Ile Leu Arg Val Glu Pro Leu Ser
                485

<210> SEQ ID NO 7
<211> LENGTH: 25
<212> TYPE: DNA
<213> ORGANISM: ARTIFICIAL
<220> FEATURE:
<223> OTHER INFORMATION: CYP4F2 SENSE PRIMER

<400> SEQUENCE: 7
ggagaggagg ttgtctggga cagac                                    25

<210> SEQ ID NO 8
<211> LENGTH: 30
<212> TYPE: DNA
<213> ORGANISM: ARTIFICIAL
<220> FEATURE:
<223> OTHER INFORMATION: CYP4F2  ANTI-SENSE PRIMER

<400> SEQUENCE: 8
acataccacg aaattcacca tttcaaagtg                                30

<210> SEQ ID NO 9
<211> LENGTH: 27
<212> TYPE: DNA
<213> ORGANISM: ARTIFICIAL
<220> FEATURE:
<223> OTHER INFORMATION: CYP4F3A SENSE PRIMER

<400> SEQUENCE: 9
agaagaaggg gagaggaggt tgtgtgg                                  27

<210> SEQ ID NO 10
<211> LENGTH: 25
<212> TYPE: DNA
<213> ORGANISM: ARTIFICIAL
<220> FEATURE:
<223> OTHER INFORMATION: CYP4F3A ANTI-SENSE PRIMER

<400> SEQUENCE: 10
cttttaaagt caccatttta ttagc                                    25

<210> SEQ ID NO 11
<211> LENGTH: 35
<212> TYPE: DNA
<213> ORGANISM: ARTIFICIAL
<220> FEATURE:
<223> OTHER INFORMATION: CYP4F3B SENSE PRIMER

<400> SEQUENCE: 11
accctcactc accacccatc tgccctgcag gatgc                         35
```

```
<210> SEQ ID NO 12
<211> LENGTH: 36
<212> TYPE: DNA
<213> ORGANISM: ARTIFICIAL
<220> FEATURE:
<223> OTHER INFORMATION: CYP4F3B ANTI-SENSE PRIMER

<400> SEQUENCE: 12
ctatgtgacc ttttgcatct gatgtctttc attcag                                    36
```

METHODS AND USES OF LEUKOTRIENE B$_4$ HYDROXYLASES TO TREAT DISEASES

CROSS-REFERENCE TO RELATED APPLICATION

This non-provisional application was published as U.S. Published Patent application 2006/0247200 A1 on Nov. 2, 2006 and claims the benefit of U.S. Provisional Application 60/676,369, filed Apr. 29, 2005, which is incorporated herein by reference in its entirety.

FIELD OF THE INVENTION

The present invention is related to methods and uses for treating or preventing diseases of humans or non-human animals by reducing the amount of active leukotriene B$_4$ (LTB$_4$) by administration of LTB$_4$ hydroxylase. In particular, the invention is directed to administration of LTB$_4$ for treating or preventing respiratory diseases caused or exacerbated by inflammation.

BACKGROUND OF THE INVENTION

Asthma is a chronic inflammatory disease of the airways. Anti-inflammatory drug therapy, primarily using corticosteroids, is now considered the first-line treatment in the management of all grades of asthma severity. Although corticosteroids are believed to be the most potent anti-inflammatory agents available, they do not suppress all inflammatory mediators involved in the asthmatic response. Leukotrienes, which are lipid mediators generated from the metabolism of arachidonic acid, play an important role in the pathogenesis of asthma. They produce bronchospasm, increase bronchial hyper-responsiveness, mucus production, and mucosal edema, and enhance airway smooth muscle cell proliferation and eosinophil recruitment into the airways, and their synthesis or release is unaffected by corticosteroid administration. The use of leukotriene synthesis inhibitors or leukotriene receptor antagonists as anti-inflammatory therapies in asthma has therefore been investigated. Beneficial effects of leukotriene-modifying drugs have been demonstrated in the management of all grades of asthma severity, and there is evidence that certain patient groups (such as those with exercise-induced asthma or aspirin-induced asthma) may be particularly suitable for such therapy (Salvi et al. (2001) Chest 119:1533-46).

Leukotriene B$_4$ (LTB$_4$), LTB$_4$ omega-hydroxylases, and human diseases.

Leukotriene B$_4$, or LTB$_4$ (chemical name: 5(S), 12(R)-dihydroxy-6,14-cis-8,10-trans-eicosatetraenoic acid), is a powerful inflammatory mediator derived from arachidonate by the actions of 5-lipoxygenese and leukotriene A$_4$ hydrolase (FIG. 1) (Samuelsson et al. (1987) Science 237:1171-76). Upon stimulation, LTB$_4$ is rapidly synthesized by inflammatory cells such as polymorphonuclear leukocytes (PMNs), macrophages, and mast cells. LTB$_4$ has been shown to exert a wide range of biological actions, such as leukocyte activation, chemotaxis, chemokinesis, release of lysosomal enzyme, production of superoxide anion, and constriction of lung parenchyma. These effects are mainly mediated by the activation of two pharmacologically distinct cell-surface LTB$_4$ receptors (BLTs). BLT$_1$ is a high-affinity receptor that has been shown to be preliminarily expressed in leukocytes, whereas BLT$_2$ is a low affinity receptor that is expressed more ubiquitously (Toda et al. (2002) Prostaglandins Other Lipid Mediat. 68-69:575-585; Yokomizo et al. (2001) Arch. Biochem. Biophys. 385:231-241). LTB$_4$ has been shown to play an important role in the pathogenesis of a variety of autoimmune disease, such as nephritis, arthritis, dermatitis, and obstructive pulmonary disease. The metabolism of LTB$_4$ leading to compounds with changed capacities to activate the BLT$_1$ and BLT$_2$ receptors is very likely of importance for the regulation of inflammation (Kikuta et al (2002) Prostaglandins Other Lipid Mediat. 68-69:345-362). LTB$_4$ can be structurally modified by different enzymatic pathways, i.e., by dehydrogenation of the 12-hydroxy group, by hydrogenation of the 10,11 double bond, by oxygenation of the omega-side chain, and by a combination of these reactions (Yokomizo et al. (2001) Arch. Biochem. Biophys. 385:231-241; Wheelan et al. (1999) Pharmacol. Exp. Ther. 288:326-334).

Hydroxylation of LTB$_4$ at the omega position is considered to be specifically catalyzed by cytochrome P450 (P450 or CYP) enzymes belonging to the CYP4F subfamily (Kikuta et al. (2002) Prostaglandins Other Lipid Mediat. 68-69:345-362; Kikuta et al. (2000) Arch. Biochem. Biophys. 383:225-232). In human PMN, LTB$_4$ is rapidly converted into 20-hydroxy-LTB$_4$ with a K$_m$ of about 0.6 micromolar (Powell (1984) J. Biol. Chem. 259:3082-3089). The human enzyme catalyzing this reaction has been identified as CYP4F3A, which also is referred to as human LTB$_4$ omega-hydroxylase (Kikuta et al., J. Biol. Chem. 268, 9376-80, 1993). Binding studies have shown that 20-hydroxy-LTB$_4$ has about the same, or even higher affinity for the BLT$_1$ receptor than 20-hydroxy-LTB$_4$, whereas it has an 18 times lower affinity for the BLT$_2$ receptor (Toda et al. (2002) Prostaglandins Other Lipid Mediat. 68-69:575-585; Wang et al. (2000) J. Biol. Chem. 275:40686-40694). The formation of 20-hydroxy-LTB$_4$ in human PMN is considered to be the first step in a catabolic pathway (Kikuta et al. (2002) Prostaglandins Other Lipid Mediat. 68-69:345-362; Wheelan et al. (1999) Pharmacol. Exp. Ther. 288:326-334). However, it is possible that 20-hydroxy-LTB$_4$, due to its discrimination between BLT$_1$ and BLT$_2$ in combination wit its changed physical properties, could play an important direct role in inflammation (Clancy et al. (1984) Proc. Natl. Acad. Sci. USA 81:5729-33). 20-hydroxy-LTB$_4$ can undergo another omega oxygenation step leading to the formation of 20-carboxy-LTB$_4$, a metabolite with decreased binding affinity for both BLT$_1$ and BLT$_2$ (Wang et al. (2000) J. Biol. Chem. 275:40686-40694). The formation of 20-hydroxy-LTB$_4$ has been described as being catalyzed by CYP4F3A, and by the action of alcohol dehydrogenase and aldehyde dehydrogenase (Kikuta et al. (2002) Prostaglandins Other Lipid Mediat. 68-69:345-62; Wheelan et al. (1999) Pharmacol. Exp. Ther. 288:326-334; Baumert et al (1989) Eur. J. Biochem 182: 223-229).

LTB$_4$ Omega-hydroxylase Genes, mRNAs, and Isoforms

Kikuta et al. (1993; J Biol Chem. 268:9376-9380) first described isolating cDNA clones for human leukotriene B4 (LTB$_4$) omega-hydroxylase (CYP4F3) expressed in human leukocytes, encoding a protein of 520 amino acids with a molecular weight of 59,805. They determined that the amino acid sequence of CYP4F3 showed 31-44% similarity to other CYP4 family members CYP4A, CYP4B, and CYP4C, but less than 25% similarity to any of the other P-450 families.

Christmas et al. (1999; J Biol Chem 274:21191-21199) cloned a novel isoform CYP4F3 (CYP4F3B) that was expressed in fetal and adult liver, but not in PMNs. They determined that, although the CYP4F3 gene contains 14 exons and 13 introns, the cDNAs for CYP4F3A (the PMN isoform) and CYP4F3B have identical coding regions, except that they contain exons 4 and 3, respectively. Both exons code for amino acids 66-114 but share only 27% identity, and both isoforms contain a total of 520 amino acids. Moreover, the K(m) of CYP4F3B is apparently 26-fold higher than the K(m) of CYP4F3A when $LTB_4$ omega-hydroxylase activity was measured using $LTB_4$ as the substrate. In addition, the 5'-termini of CYP4F3A and CYP4F3B mRNAs are derived from different parts of the CYP4F3 gene, and are initiated from distinct transcription start sites located 519 and 71 base pairs (bp), respectively, from the ATG initiation codon. A consensus TATA box is located 27 bp upstream of the CYP4F3B transcription start site, and a TATA box-like sequence is located 23 bp upstream of the CYP4F3A transcription start site. CYP4F3A inactivates LTB4 by omega-hydroxylation (Km=0.68 microm) but has low activity for arachidonic acid (Km=185 microm). CYP4F3B is selectively expressed in liver and kidney, and is the predominant CYP4F isoform in trachea and tissues of the gastrointestinal tract. CYP4F3B has a 30-fold higher Km for LTB4 compared with CYP4F3A, and is able to utilize arachidonic acid as a substrate for omega-hydroxylation (Km=22 microm) and generates 20-HETE, an activator of protein kinase C and Ca2+/calmodulin-dependent kinase II (Christmas et al. (2001) J Biol Chem. 276: 38166-38172). Thus, the tissue-specific expression of functionally distinct CYP4F3 isoforms is regulated by alternative promoter usage and mutually exclusive alternative exon splicing, result in the synthesis of two similar, but functionally distinct CYP4F3 isoforms (Christmas (2003) J Biol Chem 278:25133-25142).

Even though hydroxylation of CYP4F3A presumably occurs mainly in the PMN and in tissue infiltrated by PMNs, it is possible that metabolism in the liver also plays a role in the inactivation of $LTB_4$. In human liver, $LTB_4$ can be metabolized into 20-hydroxy-$LTB_4$ by CYP4F2 and CYP4F3B. However, CYP4F2 and CYP4F3B catalyze this reaction with Km values approximately 100 times and 30 times greater, respectively, than CYP4F3A. In the liver, 20-hydroxy-$LTB_4$ is metabolized rapidly into 20-carboxy-$LTB_4$, which can then undergo beta-oxidation leading to 18-carboxy-dinor-$LTB_4$. The human enzyme CYP4F3A, and possibly CYP4F2 and CYP4F3B, likely plays an important regulatory role during inflammation due to its involvement in $LTB_4$ omega-hydroxylation (Christmas et al. (2001) J. Biol. Chem. 276:38166-38172; Kikuta et al., (1993) J. Biol. Chem. 268:9376-9380; Kikuta et al. (1994) FEBS Lett. 348:7074; Kikuta et al. (2002) Prostaglandins Other Lipid Mediat. 68-69:345-362; Hankin et al. (1998) J. Pharmacol. Exp. Ther. 285:155-161; Wheelan et al. (1999) Pharmacol. Exp. Ther. 288:326-334; Bylund et al. (2003) Arch Biochem Biophys 412:34-41).

CYP4F3A is the most tissue specific and most efficient $LTB_4$ omega-hydroxylase, judging from its restricted localization in human polymorphonuclear leukocytes (PMN) and its very low Km value for $LTB_4$. In contrast, CYP4F2 is widely distributed in human liver and other tissues, and catalyzes omega-hydroxylation of various lipoxygenase-derived eicosanoids as well as $LTB_4$, with relatively comparable and high Km values. CYP4F3B is very similar to CYP4F2 in its tissue localization and its Km value for $LTB_4$ (Kikuta et al. (2002) Prostaglandins Other Lipid Mediat. 68-69:345-362). Until recently, it was believed that CYP4F3 was the only $LTB_4$ omega-hydroxylase expressed in PMNs, and hence, to the degree that $LTB_4$ contributed to asthma, it would be presumed that CYP4F3 would be most responsible for modulating its effects. However, Kikuta et al. (2004; Biochim Biophys Acta. 1683:7-15) have provided evidence that PMNs also express CYP4F3B in addition to CYP4F3A. Moreover, the transcription start site of CYP4F3B mRNA in PMNs is identical to that of CYP4F3 (i.e., CYP4F3A) mRNA (Kikuta et al. (2004) Biochim Biophys Acta. 1683 (1-3):7-15). They also provided evidence that CYP4F3A is expressed at low levels in a population of peripheral blood monocytes.

There are at least four rat CYP4F enzymes, which have been designated CYP4F1 CYPF4, CYP4F5, and CYP4F6. There is significant amino acid sequence homology between mammalian CYP4F proteins. For example, the human CYP4F2, CYP4F3a, and CYP4Fb enzymes differ in amino acid sequence by 87 to 92%. Similarly, the rat CYP4F5 and CYP4F6 enzymes are 79% homologous. In addition, there is fairly substantial amino acid sequence homology between the human enzymes (CYP4F2, CYP4F3a, and CYP4Fb) and the rat enzymes (CYP4F5 and CYP4F6), which range in homology from 71% (human CYP4F2 vs rat CYP4F5) to 76% (human CYP4F3b vs rat CYP4F6). It is not surprising then, considering these amino acid sequence similarities, that each of the four rat isoforms of CYP4F (i.e., CYP4F1 CYPF4, CYP4F5, and CYP4F6), like their human counterparts, are known to catalyze the omega-hydroxylation of $LTB_4$ CYP4F1 and CYP4F4 also catalyze the omega-hydroxylation of arachidonic acid. Like the CYP4F3 isoforms in humans, CYP4F1 catalyzes the omega-hydroxylation of $LTB_4$ to form 20-hydroxyl-$LTB_4$. The rat CYP4F5 and CYP4F6 isoforms catalyze the omega-hydroxylation of $LTB_4$ to hydroxylated forms of $LTB_4$ not reported in humans. CYP4F5 omega-hydroxylates $LTB_4$ to form 18-hydroxyl-$LTB_4$, and CYP4F6 omega-hydroxylates $LTB_4$ to form 18-hydroxyl-$LTB_4$, and 19-18-hydroxyl-$LTB_4$ (Bylund et al. (2003) Arch. Biochem. Biophys. 412:34-41; Chen and Hardwick (1993) Arch. Biochem. Biophys. 300:18-23; Kawashima and Strobel (1995) Biochem. Biophys. Res. Commun. 217:1137-1144; Xu et al. (2004) J. Pharmacol. Exp. Ther. 308:887-895).

The enzymatic activities of leukotriene B4 hydroxylase may be enhanced in the presence of an enzyme, NADPH-cytochrome P-450 reductase, which can convert oxidized forms of leukotriene B4 hydroxylases to reduced forms. NADPH-cytochrome P-450 reductase, which is oxidized in the process of reducing leukotriene B4 hydroxylase, can in turn be converted to a reduced form in the presence of a reduced form of nicotinamide adenine dinucleotide phosphate (NADPH). In the process of reducing NADPH-cytochrome P-450 reductase, NADPH is converted to an oxidized form (NADP+) (Sumimoto et al. (1988) Eur J Biochem. 172(2):315-324); Nisimoto et al. (1994) Biochem J. 297:585-593; Mukhtar et al. (1989) Xenobiotica 19:151-159; Kikuta Y et al. (1998) Arch Biochem Biophys 355: 201-205; Bylund et al. (2003) Arch Biochem Biophys 412: 34-41).

SUMMARY OF THE INVENTION

The present invention utilizes human $LTB_4$ hydroxylase protein, as well as analogs and variants thereof, that have an $LTB_4$ hydroxylation activity. As is characteristic of $LTB_4$ hydroxylase proteins in general, the human $LTB_4$ hydroxylase useful in the present invention is a cytochrome P450 enzyme that catalyzes the hydroxylation of arachidonic acid and/or its derivatives, such as the omega-hydroxylation of $LTB_4$.

The invention provides methods for reducing amount of LTB$_4$ in a patient, comprising administering a therapeutically effective dose of human LTB$_4$ hydroxylase to the patient. The invention is particularly directed to a method of treating a patient having a disease such as asthma, cystic fibrosis, chronic bronchitis, pneumonia, bronchiectasis, emphysema, or systemic lupus erythematosus, that comprises administering a therapeutically effective amount of human LTB$_4$ hydroxylase to the patient. The invention also is directed to the use of human LTB$_4$ hydroxylase in vitro, such as for hydroxylating LTB$_4$ that is present in a biological specimen or other material, and in diagnostic and other assays. In certain embodiments, a leukotriene B$_4$ hydroxylase is administered in combination with nicotinamide adenine dinucleotide phosphate, an NADPH-cytochrome P-450 reductase, or combinations thereof.

The invention utilizes nucleic acids encoding human LTB$_4$ hydroxylase, recombinant vectors comprising such nucleic acids, and recombinant host cells transformed with those nucleic acids or vectors. The invention encompasses the use of such nucleic acids and vectors for in vivo or ex vivo gene therapy. The invention also provides pharmaceutical compositions comprising human LTB$_4$ hydroxylase, optionally together with a pharmaceutically acceptable excipient/carrier. Such pharmaceutical compositions may, alternatively, further comprise nicotinamide adenine dinucleotide phosphate, an NADPH-cytochrome P-450 reductase, or combinations thereof.

These and other aspects of the invention will be apparent to the ordinary skilled artisan upon consideration of the following detailed description.

DETAILED DESCRIPTION OF THE INVENTION

The various aspects of the present invention are accomplished by first providing isolated DNA comprising the nucleotide coding sequences for human LTB$_4$ hydroxylases (SEQ ID NOs 1, 3, and 5). By providing the full nucleotide coding sequence for human LTB$_4$ hydroxylase, the invention enables the production of human LTB$_4$ hydroxylase by means of recombinant DNA technology, thereby making available sufficient quantities of substantially pure human LTB$_4$ hydroxylase protein for therapeutic and diagnostic use.

As used herein, the term "human LTB$_4$ hydroxylase" refers to the polypeptide having the amino acid sequence of the mature protein set forth in SEQ ID NOs 2, 4, and 6, as well as modified and variant forms thereof as described herein. Modified and variant forms of human LTB$_4$ hydroxylase are produced in vitro by means of chemical or enzymatic treatment or in vivo by means of recombinant DNA technology. Such polypeptides differ from human LTB$_4$ hydroxylase, for example, by virtue of one or more amino acid substitutions, insertions, and/or deletions, or in the extent or pattern of glycosylation, but in all cases will possess LTB$_4$ hydroxylase activity. A "variant" or "amino acid sequence variant" of human LTB$_4$ hydroxylase is a polypeptide that comprises an amino acid sequence different from that of human LTB$_4$ hydroxylase. Generally, a variant will have at least 70% sequence identity, preferably at least 90% sequence identity, more preferably at least 95% sequence identity, and most preferably at least 98% sequence identity with human LTB$_4$ hydroxylase. Percentage sequence identity is determined, for example, by the Fitch, et al., Proc. Natl. Acad. Sci. USA 80:1382-1386 (1983), version of the algorithm described by Needleman, et al., J. Mol. Biol. 48:443-453 (1970), after aligning the sequences to provide for maximum homology. Such variants include naturally occurring allelic forms of human LTB$_4$ hydroxylase that are of human origin as well as naturally occurring homologs of human LTB$_4$ hydroxylase that are found in other animal species.

Figure 3:
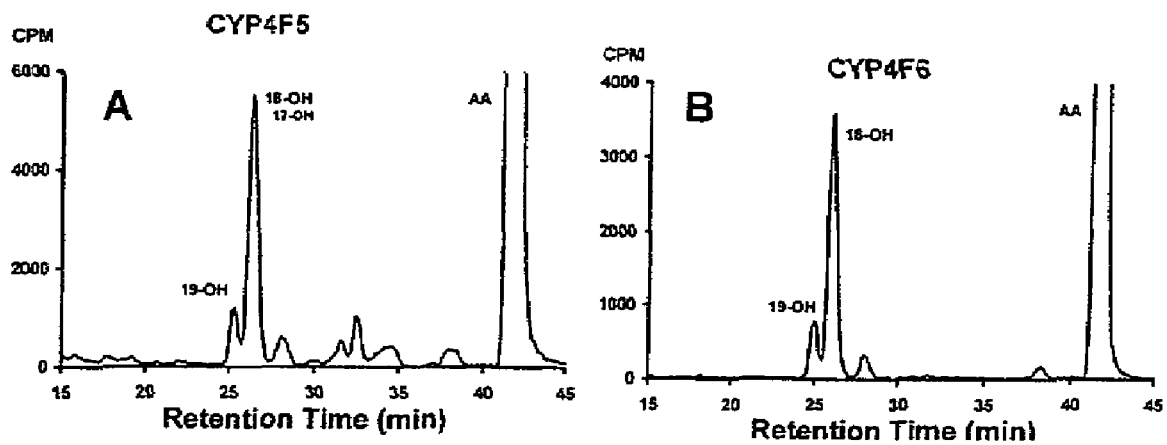
FIG. 3. The figure illustrates the hydroxylation of arachidonic acid (AA) by recombinant forms of the rat LTB$_4$ hydroxylases CYP4F5 and CYP4F6. Depicted are chromatograms of AA, 18-hydroxyl-AA, and 19-hydroxyl-AA resolved by RP-HPLC following incubation of AA with either CYP4F5 (A), or CYP4F6 (B).

"Human LTB$_4$ hydroxylase activity" refers to the enzymatic activity of LTB$_4$ human LTB4 hydroxylase in causing a hydroxyl group to be added to LTB4. The human forms of LTB$_4$ hydroxylase are known to cause hydroxylation at the omega position of LTB$_4$, resulting in the formation of 20-hydroxy-LTB$_4$. Other mammalian forms are known to catalyze hydroxylation of LTB$_4$ yielding 18-hydroxy-LTB$_4$, and 19-hydroxy-LTB$_4$. LTB$_4$ hydroxylase activity is readily determined by any of several different methods known in the art, including biochemical assays for enzyme activity by which the products of LTB$_4$ hydroxylase activity are analyzed by reverse-phase high-performance liquid chromatography (RP-HPLC), or liquid-chromatography-mass spectrometry (LC-MS) (Bylund and Harder, Arch. Biochem. and Biophys. 412:3441 (2003)). In some instances, LTB$_4$ hydroxylase activity is assayed by monitoring the hydroxylation of a known substrate of the enzyme, such as arachidonic acid (AA) (FIG. 3).

For convenience, substitutions, insertions, and/or deletions in the amino acid sequence of human LTB$_4$ hydroxylase are usually made by introducing mutations into the corresponding nucleotide sequence of the DNA encoding human LTB$_4$ hydroxylase, for example by site-directed mutagenesis. Expression of the mutated DNA then results in production of the variant human LTB$_4$ hydroxylase, having the desired amino acid sequence.

Whereas any technique known in the art can be used to perform site-directed mutagenesis, e.g. as disclosed in Sambrook, et al., Molecular Cloning: A Laboratory Manual, Second Edition (Cold Spring Harbor Laboratory Press, New York (1989)), oligonucleotide-directed mutagenesis is the preferred method for preparing the human LTB$_4$ hydroxylase variants of this invention. This method, which is well known in the art (Zoller, et al., Meth. Enzymol. 100:4668-

500 (1983); Zoller, et al., Meth. Enzymol. 154:329-350 (1987); Carter, Meth. Enzymol. 154:382-403 (1987); Kunkel, et al., Meth. Enzymol. 154:367-382 (1987); Horwitz, et al., Meth. Enzymol. 185:599-611 (1990)), is particularly suitable for making substitution variants, although it may also be used to conveniently prepare deletion and insertion variants, as well as variants having multiple substitution, insertion, and/or deletion mutations.

Briefly, in carrying out site-directed mutagenesis of DNA encoding human $LTB_4$ hydroxylase (or a variant thereof), the DNA is altered by first hybridizing an oligonucleotide encoding the desired mutation to a single strand of the DNA. After hybridization, a DNA polymerase is used to synthesize an entire second strand, using the hybridized oligonucleotide as a primer, and using the single strand of the DNA as a template. Thus, the oligonucleotide encoding the desired mutation is incorporated in the resulting double-stranded DNA.

Oligonucleotides may be prepared by any suitable method, such as by purification of a naturally occurring DNA or by in vitro synthesis. For example, oligonucleotides are readily synthesized using various techniques in organic chemistry, such as described by Narang, et al., Meth. Enzymol. 68:90-98 (1979); Brown, et al., Meth. Enzymol. 68:109-151 (1979); Caruthers, et al., Meth. Enzymol. 154: 287-313 (1985). The general approach to selecting a suitable oligonucleotide for use in site-directed mutagenesis is well known. Typically, the oligonucleotide will contain 10-25 or more nucleotides, and will include at least 5 nucleotides on either side of the sequence encoding the desired mutation so as to ensure that the oligonucleotide will hybridize preferentially at the desired location to the single-stranded DNA template molecule.

"Polymerase chain reaction," or "PCR," generally refers to a method for amplification of a desired nucleotide sequence in vitro, as described, for example, in U.S. Pat. No. 4,683,195. In general, the PCR method involves repeated cycles of primer extension synthesis, using oligonucleotide primers capable of hybridizing preferentially to a template nucleic acid.

PCR mutagenesis (Higuchi, in PCR Protocols, pp. 177-183 (Academic Press, 1990); Vallette, et al., Nuc. Acids Res. 17:723-733 (1989)) is also suitable for making the variants of human $LTB_4$ hydroxylase. Briefly, when small amounts of template DNA are used as starting material in a PCR, primers that differ slightly in sequence from the corresponding region in the template DNA can be used to generate relatively large quantities of a specific DNA fragment that differs from the template sequence only at the positions where the primers differ from the template. For introduction of a mutation into a plasmid DNA, for example, the sequence of one of the primers includes the desired mutation and is designed to hybridize to one strand of the plasmid DNA at the position of the mutation; the sequence of the other primer must be identical to a nucleotide sequence within the opposite strand of the plasmid DNA, but this sequence can be located anywhere along the plasmid DNA. It is preferred, however, that the sequence of the second primer is located within 200 nucleotides from that of the first, such that in the end the entire amplified region of DNA bounded by the primers can be easily sequenced. PCR amplification using a primer pair like the one just described results in a population of DNA fragments that differ at the position of the mutation specified by the primer, and possibly at other positions, as template copying is somewhat error-prone. Wagner, et al., in PCR Topics, pp. 69-71 (Springer-Verlag, 1991).

If the ratio of template to product amplified DNA is extremely low, the majority of product DNA fragments incorporate the desired mutations). This product DNA is used to replace the corresponding region in the plasmid that served as PCR template using standard recombinant DNA methods. Mutations at separate positions can be introduced simultaneously by either using a mutant second primer, or performing a second PCR with different mutant primers and ligating the two resulting PCR fragments simultaneously to the plasmid fragment in a three (or more)-part ligation.

Another method for preparing variants, cassette mutagenesis, is based on the technique described by Wells et al., Gene, 34:315-323 (1985). The starting material is the plasmid (or other vector) comprising the DNA sequence to be mutated. The codon(s) in the starting DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the DNA. The plasmid DNA is cut at these sites to linearize it. A double-stranded oligonucleotide encoding the sequence of the DNA between the restriction sites but containing the desired mutation(s) is synthesized using standard procedures, wherein the two strands of the oligonucleotide are synthesized separately and then hybridized together using standard techniques. This double-stranded oligonucleotide is referred to as the cassette. This cassette is designed to have 5' and 3' ends that are compatible with the ends of the linearized plasmid, such that it can be directly ligated to the plasmid. The resulting plasmid contains the mutated DNA sequence.

The presence of mutation(s) in a DNA is determined by methods well known in the art, including restriction mapping and/or DNA sequencing. A preferred method for DNA sequencing is the dideoxy chain termination method of Sanger, et al., Proc. Natl. Acad. Sci. USA 72:3918-3921 (1979).

DNA encoding human $LTB_4$ hydroxylase is inserted into a replicable vector for further cloning or expression. "Vectors" are plasmids and other DNAs that are capable of replicating within a host cell, and as such, are useful for performing two functions in conjunction with compatible host cells (a vector-host system). One function is to facilitate the cloning of nucleic acid that encodes human $LTB_4$ hydroxylase, i.e., to produce usable quantities of the nucleic acid. The other function is to direct the expression of human $LTB_4$ hydroxylase. One or both of these functions are performed by the vector in the particular host cell used for cloning or expression. The vectors will contain different components depending upon the function they are to perform.

It is possible to cause the synthesis of specific mRNAs in a cell by introducing into the cell a DNA gene expression vector, such as a plasmid, episome, or viral DNA or RNA molecule (e.g. certain recombinant adenoviruses, herpesviruses, SV40 viruses, RNA viruses), or a virus capable of causing such DNA pr RNA molecules to be produced in cells (such as a retrovirus, i.e., a recombinant HIV). In the present invention, such vectors would contain the coding sequence of a human $LTB_4$ hydroxylase, and genetic signals (promoters and enhancers) that would cause RNA to be synthesized when introduced into an organism. More specifically, the cells being targeted would be those cells in the lungs, or in locations in the body that may require a reduction in $LTB_4$. It is possible for those of ordinary skill in the arts to produce such vectors, e.g., adenovirus vectors that produce enzymatically active cytochrome P450 enzymes in vitro (Medhora et al., Am. J. Physiol. Heart Circ. Physiol. 284:H215-H224, (2003)).

The human $LTB_4$ hydroxylase of the present invention may be expressed in the form of a preprotein wherein the $LTB_4$ hydroxylase includes a leader or signal sequence, or may be in the form of a mature protein which lacks a leader or signal sequence. The human $LTB_4$ hydroxylase also may be in the form of a fusion protein wherein additional amino acid residues are covalently joined to the amino- or carboxy-terminus of the preprotein or mature form of the DNase.

To produce human $LTB_4$ hydroxylase, an expression vector will comprise DNA encoding human $LTB_4$ hydroxylase, as described above, operably linked to a promoter and a ribosome binding site. The human $LTB_4$ hydroxylase then is expressed directly in recombinant cell culture, or as a fusion with a heterologous polypeptide, preferably a signal sequence or other polypeptide having a specific cleavage site at the junction between the heterologous polypeptide and the human $LTB_4$ hydroxylase amino acid sequence.

"Operably linked" refers to the covalent joining of two or more DNA sequences, by means of enzymatic ligation or otherwise, in a configuration relative to one another such that the normal function of the sequences can be performed. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. Linking is accomplished by ligation at convenient restriction sites. If such sites do not exist, then synthetic oligonucleotide adaptors or linkers are used, in conjunction with standard recombinant DNA methods.

Prokaryotes (e.g., *E. coli*, strains of *Bacillus, Pseudomonas*, and other bacteria) are the preferred host cells for the initial cloning steps of this invention. They are particularly useful for rapid production of large amounts of DNA, for production of single-stranded DNA templates used for site-directed mutagenesis, and for DNA sequencing of the variants generated. Prokaryotic host cells also may be used for expression of DNA encoding human $LTB_4$ hydroxylase. Polypeptides that are produced in-prokaryotic cells typically will be non-glycosylated.

In addition, human $LTB_4$ hydroxylase may be expressed in eukaryotic host cells, including eukaryotic microbes (e.g., yeast) or cells derived from an animal or other multicellular organism (e.g., Chinese hamster ovary cells, and other mammalian cells), or in live animals (e.g., cows, goats, sheep). Insect cells and fungi also may be used.

Cloning and expression methodologies are well known in the art. Examples of prokaryotic and eukaryotic host cells, and starting expression vectors, suitable for use in producing human $LTB_4$ hydroxylase are, for example, those disclosed in Shak, PCT Patent Publication No. WO 90/07572, published Jul. 12, 1990. To obtain expression of human $LTB_4$ hydroxylase, an expression vector of the invention is introduced into host cells by transformation or transfection, and the resulting recombinant host cells are cultured in conventional nutrient media, modified as appropriate for inducing promoters, selecting recombinant cells, or amplifying human $LTB_4$ hydroxylase DNA. The culture conditions, such as temperature, pH, and the like, are those previously used with the host cell, and as such will be apparent to the ordinarily skilled artisan.

"Transformation" and "transfection" are used interchangeably to refer to the process of introducing DNA into a cell. Following transformation or transfection, the DNA may integrate into the host cell genome, or may exist as an extrachromosomal element. If prokaryotic cells or cells that contain substantial cell wall constructions are used as hosts, the preferred methods of transfection of the cells with DNA is the calcium treatment method described by Cohen et al., Proc. Natl. Acad. Sci. 69:2110-2114 (1972) or the polyethylene glycol method of Chung et al., Nuc. Acids. Res. 16:3580 (1988). If yeast are used as the host, transfection is generally accomplished using polyethylene glycol, as taught by Hinnen, Proc. Natl. Acad. Sci. U.S.A., 75: 1929-1933 (1978). If mammalian cells are used as host cells, transfection generally is carried out by the calcium phosphate precipitation method, Graham, et al., Virology 52:546 (1978), Gorman, et al., DNA and Protein Eng. Tech. 2:3-10 (1990). However, other known methods for introducing DNA into prokaryotic and eukaryotic cells, such as nuclear injection, electroporation, lipofection, or protoplast fusion also are suitable for use in this invention.

Particularly useful in this invention are expression vectors that provide for the transient expression in mammalian cells of DNA encoding human $LTB_4$ hydroxylase. In general, transient expression involves the use of an expression vector that is able to efficiently replicate in a host cell, such that the host cell accumulates many copies of the expression vector and, in turn, synthesizes high levels of a desired polypeptide encoded by the expression vector. Transient expression systems, comprising a suitable expression vector and a host cell, allow for the convenient positive identification of polypeptides encoded by cloned DNAs, as well as for the rapid screening of such polypeptides for desired biological or physiological properties. Wong, et al., Science 228:810-815 (1985); Lee, et al., Proc. Nat Acad. Sci. USA 82:4360-4364 (1985); Yang, et al., Cell 47:3-10 (1986). Thus, transient expression systems are conveniently used for expressing the DNA encoding amino acid sequence variants of human $LTB_4$ hydroxylase, in conjunction with assays to identify those variants that have such useful properties as increased half-life or decreased immunogenicity in vivo, or increased $LTB_4$ hydroxylase activity at physiological pH.

Human $LTB_4$ hydroxylase preferably is secreted from the host cell in which it is expressed, in which case the variant is recovered from the culture medium in which the host cells are grown. In that case, it may be desirable to grow the cells in a serum free culture medium, since the absence of serum proteins and other serum components in the medium may facilitate purification of the variant. If it is not secreted, then the human $LTB_4$ hydroxylase is recovered from lysates of the host cells. When the human $LTB_4$ hydroxylase is expressed in a host cell other than one of human origin, the variant will be completely free of proteins of human origin. In any event, it will be necessary to purify the human $LTB_4$ hydroxylase from recombinant cell proteins in order to obtain substantially homogeneous preparations of the human $LTB_4$ hydroxylase. For therapeutic uses, the purified human $LTB_4$ hydroxylase preferably will be greater than 99% pure (i.e., any other proteins will comprise less than 1% of the total protein in the purified composition).

Figure 1:
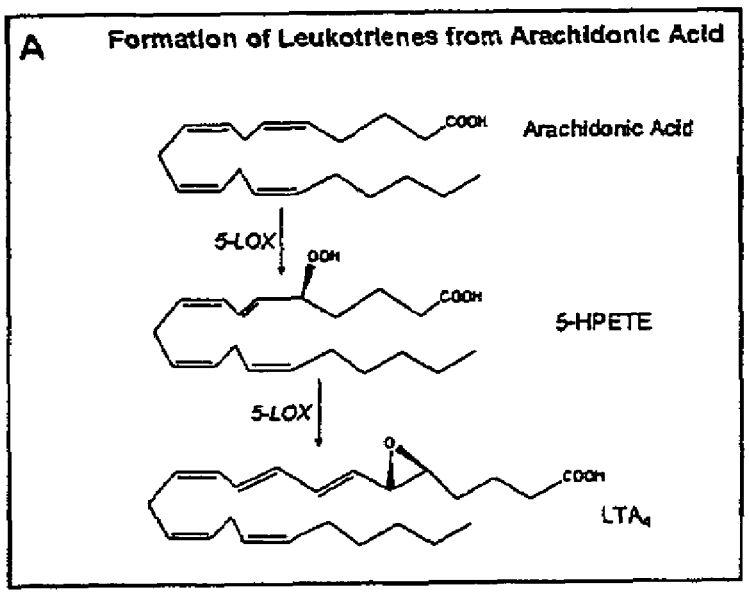
FIG. 1. Synthesis and Metabolism of LTB$_4$ from Arachidonic Acid. A) Once released from lipid stores, arachidonic acid may be metabolized by 5-lipoxygenase (5-LOX) to form the intermediate 5-HPETE and then leukotriene A$_4$ (LTA$_4$). B) LTA$_4$ may then be metabolized to LTB$_4$ or converted to the cysteinyl-leukotrienes LTC$_4$ and LTD$_4$. C) Metabolism of LTB$_4$ Occurs by Hydroxylation at the 18 and/or 19 Position by the Rat Enzymes CYP 4F5 and 4F6.
Figure 1:
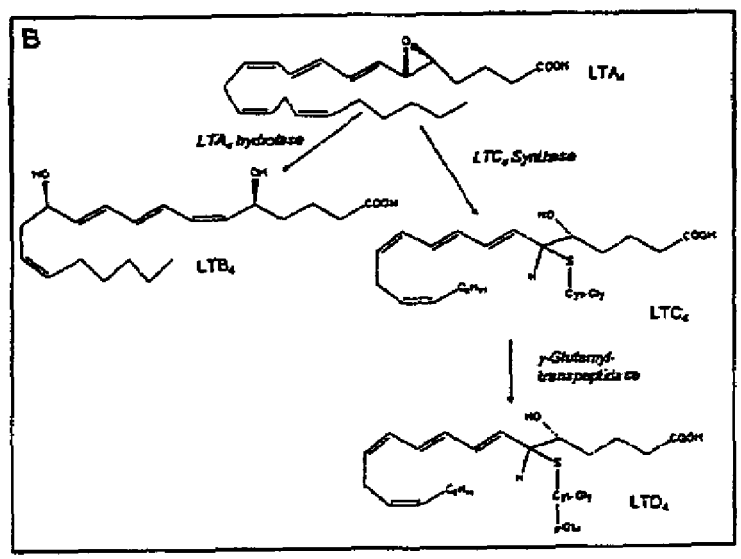
Figure 1:
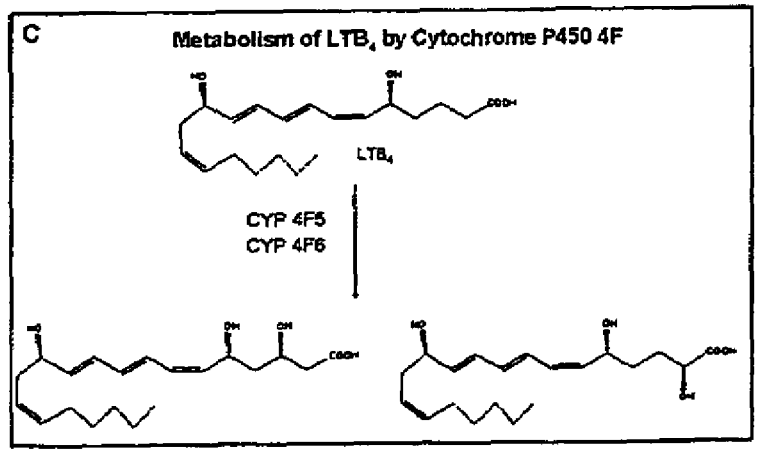

It is further contemplated that human $LTB_4$ hydroxylase may be produced by a method involving homologous recombination and amplification, for example, as described in PCT Patent Publication No. WO 91/06667, published May 16, 1991. Briefly, this method involves transforming cells containing an endogenous gene encoding human $LTB_4$ hydroxylase with a homologous DNA, which homologous DNA comprises (1) an amplifiable gene (e.g., a gene encoding dihydrofolate reductase (DHFR)), and (2) at least one flanking sequence, having a length of at least about 150 base pairs, which is homologous with a nucleotide sequence in the cell genome that is within or in proximity to the gene encoding human $LTB_4$ hydroxylase. The transformation is carried out under conditions such that the homologous DNA integrates into the cell genome by recombination. Cells having integrated the homologous DNA then are subjected to conditions which select for amplification of the amplifiable gene, whereby the human $LTB_4$ hydroxylase gene amplified concomitantly. The resulting cells then are screened for production of desired amounts of human $LTB_4$ hydroxylase. Flanking sequences that are in proximity to a gene encoding human $LTB_4$ hydroxylase are readily identified, for example, by the method of genomic walking, using as a starting point the nucleotide sequence of human $LTB_4$ hydroxylase shown in FIG. 1. Spoerel, et al., Meth. Enzymol. 152:598-603 (1987).

Generally, purification of human $LTB_4$ hydroxylase is accomplished by taking advantage of the differential physicochemical properties of the human $LTB_4$ hydroxylase as compared to the contaminants with which it may be associated. For example, as a first step, the culture medium or host cell lysate is centrifuged to remove particulate cell debris. The human $LTB_4$ hydroxylase thereafter is purified from contaminant soluble proteins and polypeptides, for example, by ammonium sulfate or ethanol precipitation, gel filtration (molecular exclusion chromatography), ion-exchange chromatography, hydrophobic chromatography, immunoaffinity chromatography (e.g., using a column comprising anti-human $LTB_4$ hydroxylase antibodies coupled to Sepharose), tentacle cation exchange chromatography (Frenz, et al., U.S. Pat. No. 5,279,823, issued Jan. 18, 1994), reverse phase HPLC, and/or gel electrophoresis.

In some host cells (especially bacterial host cells) the human $LTB_4$ hydroxylase may be expressed initially in an insoluble, aggregated form (referred to in the art as "refractile bodies" or "inclusion bodies") in which case it will be necessary to solubilize and renature the human $LTB_4$ hydroxylase in the course of its purification. Methods for solubilizing and renaturing recombinant protein refractile bodies are known in the art (see e.g., Builder, et al., U.S. Pat. No. 4,511,502, issued Apr. 16, 1985).

In another embodiment of this invention, covalent modifications are made directly to human $LTB_4$ hydroxylase to give it a desired property (for example, increased half-life or decreased immunogenicity in vivo, or increased $LTB_4$ hydroxylase activity at physiological pH), and may be made instead of or in addition to the amino acid sequence substitution, insertion, and deletion mutations described above.

Covalent modifications are introduced by reacting targeted amino acid residues of human $LTB_4$ hydroxylase with an organic derivatizing agent that is capable of reacting with selected amino acid side-chains or N- or C-terminal residues. Suitable derivatizing agents and methods are well known in the art. Covalent coupling of glycosides to amino acid residues of the protein may be used to modify or increase the number or profile of carbohydrate substituents.

The covalent attachment of agents such as polyethylene glycol (PEG) or human serum albumin to human $LTB_4$ hydroxylase may reduce immunogenicity and/or toxicity of the human $LTB_4$ hydroxylase and/or prolong its half-life, as has been observed with other proteins. Abuchowski, et al., J. Biol. Chem. 252:3582-3586 (1977); Poznansky, et al., FEBS Letters 239:18-22 (1988); Goodson, et al., Biotechnology 8:343-346 (1990); Katre, J. Immunol. 144:209-213 (1990); Harris, Polyethylene Glycol Chemistry (Plenum Press, 1992). As another example, the variant or modified form of human $LTB_4$ hydroxylase may comprise an amino acid sequence mutation or other covalent modification that reduces the susceptibility of the variant to degradation by proteases (e.g., neutrophil elastase) that may be present in sputum and other biological materials, as compared to human $LTB_4$ hydroxylase.

Antibodies to human $LTB_4$ hydroxylase are produced by immunizing an animal with human $LTB_4$ hydroxylase or a fragment thereof, optionally in conjunction with an immunogenic polypeptide, and thereafter recovering antibodies from the serum of the immunized animals. Alternatively, monoclonal antibodies are prepared from cells of the immunized animal in conventional fashion. The antibodies also can be made in the form of chimeric (e.g., humanized) or single chain antibodies or Fab fragments, using methods well known in the art. Preferably, the antibodies will bind to human $LTB_4$ hydroxylase but will not substantially bind to (i.e., cross react with) other cytochrome P450 enzymes. The antibodies can be used in methods relating to the localization and activity of human $LTB_4$ hydroxylase, for example, for detecting human $LTB_4$ hydroxylase and measuring its levels in tissues or clinical samples. Immobilized anti-human $LTB_4$ hydroxylase antibodies would be particularly useful in the detection of human $LTB_4$ hydroxylase in clinical samples for diagnostic purposes, and in the purification of human $LTB_4$ hydroxylase.

Purified human $LTB_4$ hydroxylase could be used to reduce the amount of active $LTB_4$ in the respiratory system. As a result, human $LTB_4$ hydroxylase would be useful for reducing inflammation, or the undesirable influx of immune system cells (e.g. neutrophils) into the respiratory systems of patients suffering from acute or chronic bronchial pulmonary diseases, including asthma, infectious pneumonia, bronchitis or tracheobronchitis, bronchiectasis, cystic fibrosis, tuberculosis, and fungal infections. For such therapies, a solution or finely divided dry preparation of the human $LTB_4$ hydroxylase is instilled in conventional fashion into the airways (e.g., bronchi) or lungs of a patient, for example by aerosolization. Alternatively, human $LTB_4$ hydroxylase is prepared as an aqueous suspension and administered by inhalation of fine-droplets formed by neubulization.

Human $LTB_4$ hydroxylase also is useful for conditions that would benefit, at some stage of treatment, from a reduction in inflammation, or the influx of immune system cells attracted by $LTB_4$. Such conditions and their treatment would include adjunctive treatment of abscesses or severe closed-space infections in conditions such as empyema, meningitis, abscess, peritonitis, sinusitis, otitis, periodontitis, pericarditis, pancreatitis, cholelithiasis, endocarditis and septic arthritis, as well as in topical treatments in a variety of inflammatory and infected lesions such as infected lesions of the skin and/or mucosal membranes, surgical wounds, ulcerative lesions and burns. Human $LTB_4$ hydroxylase may improve the efficacy of antibiotics used in the treatment of such infections (e.g., gentamicin activity is markedly reduced by reversible binding to intact DNA).

Human $LTB_4$ hydroxylase also is useful for preventing the new development and/or exacerbation of respiratory infections, such as may occur in patients having acute or chronic asthma, cystic fibrosis, chronic bronchitis, pneumonia, or other pulmonary disease, or patients whose breathing is assisted by ventilator or other mechanical device, or other patients at risk of developing respiratory infections, for example post-surgical patients.

Finally, human LTB4 hydroxylase is useful for the treatment of other non-infected conditions complicated by the influx of immune system cells attracted by the presence of $LTB_4$.

Human $LTB_4$ hydroxylase can be formulated according to known methods to prepare therapeutically useful compositions. Typically, the human $LTB_4$ hydroxylase is formulated with a physiologically acceptable excipient (or carrier) for therapeutic use. Such excipients are used, for example, to provide liquid formulations and sustained-release formulations of human $LTB_4$ hydroxylase. The human $LTB_4$ hydroxylase formulation may be used with commercially-available nebulizers including jet nebulizers and ultrasonic nebulizers for administration of the $LTB_4$ hydroxylase directly into the airways or lungs of an affected patient. Another preferred therapeutic composition is a dry powder of human $LTB_4$ hydroxylase, preferably prepared by spray-drying of a solution of the human $LTB_4$ hydroxylase. In all cases, it is desirable that the therapeutic compositions of $LTB_4$ hydroxylase be sterile. Preferably, the therapeutic compositions are disposed in a container fabricated of plastic or other non-glass material that does not readily adsorb proteins.

In a further embodiment, the therapeutic composition comprises cells actively producing human $LTB_4$ hydroxylase. Such cells may be directly introduced into the tissue of a patient, or may be encapsulated within porous membranes which are then implanted in a patient (see e.g., Aebischer, et al., U.S. Pat. No. 4,892,538, issued Jan. 9, 1990; Aebischer, et al., U.S. Pat. No. 5,283,187, issued Feb. 1, 1994), in either case providing for the delivery of the human $LTB_4$ hydroxylase into areas within the body of the patient in need of increased concentrations of $LTB_4$ hydroxylase activity. In one embodiment of the invention, the patient's cells are transformed, either in vivo or ex vivo, with DNA encoding human $LTB_4$ hydroxylase, and then used to produce the human $LTB_4$ hydroxylase directly within the patient. This latter method is commonly referred to as gene therapy. In another embodiment, the patient's cells are transformed with other DNA (such as a promoter, enhancer, or amplifiable gene) that is capable of activating or increasing expression of an endogenous human $LTB_4$ hydroxylase gene.

In certain circumstances, it may be desirable to decrease the amount of human $LTB_4$ hydroxylase expressed in a cell. For that purpose, human $LTB_4$ hydroxylase anti-sense oligonucleotides can be made and a method utilized for diminishing the level of human $LTB_4$ hydroxylase within the cell comprising introducing into the cell one or more human $LTB_4$ hydroxylase anti-sense oligonucleotides. The term "human $LTB_4$ hydroxylase anti-sense oligonucleotide" refers to an oligonucleotide that has a nucleotide sequence that is capable of interacting through base pairing with a complementary nucleotide sequence that is involved in the expression of human $LTB_4$ hydroxylase within a cell, and thereby interfering with such expression.

The $LTB_4$ hydroxylases or $LTB_4$ hydroxylase-expressing vectors of this invention can be used therapeutically to reduce or block the activity of $LTB_4$, and thereby to treat any medical condition caused or mediated by $LTB_4$. The dosage regimen involved in a therapeutic application will be determined by the attending physician, considering various factors which may modify the action of the therapeutic substance, e.g., the condition, body weight, sex and diet of the patient, the severity of any infection, time of administration, and other clinical factors. The therapeutically effective amount of human $LTB_4$ hydroxylase will depend, for example, upon the amount of $LTB_4$ in the material to be treated, the therapeutic objectives, the route of administration, and the condition of the patient. Accordingly, it will be necessary for the therapist to titer the dosage and modify the route of administration as required to obtain the optimal therapeutic effect. Generally, the therapeutically effective amount of human $LTB_4$ hydroxylase will be a dosage of from about 0.1 microgram to about 5 mg of the variant per kilogram of body weight of the patient, administered within pharmaceutical compositions, as described herein.

Typical protocols for the therapeutic administration of such substances are well known in the art. Administration of the compositions of this invention is typically by aerosol, but other routes of administration are also employed including by parenteral, intraperitoneal, intravenous, subcutaneous, or intramuscular injection, or by infusion or by any other acceptable systemic method. Often, treatment dosages are titrated upward from a low level to optimize safety and efficacy. Generally, daily dosages will fall within a range of about 0.01 to 20 mg protein per kilogram of body weight. Typically, the dosage range will be from about 0.1 to 5 mg per kilogram of body weight. Dosages will be adjusted to account for the molecular sizes and possibly decreased half-lives (clearance times) following administration. An "effective amount" of a composition of the invention is an amount that will ameliorate one or more of the well-known parameters that characterize medical conditions caused or mediated by $LTB_4$.

Therapeutic formulations may be administered in many conventional dosage formulation. Formulations typically comprise at least one active ingredient, together with one or more pharmaceutically acceptable carriers. Formulations may include those suitable for aerosol, oral, rectal, nasal, or parenteral (including subcutaneous, intramuscular, intravenous and intradermal) administration.

Although the compositions of this invention could be administered in simple solution, they are more typically used in combination with other materials such as carriers, preferably pharmaceutical carriers. Useful pharmaceutical carriers can be any compatible, non-toxic substances suitable for delivering the compositions of the invention to a patient. Sterile water, alcohol, fats, waxes, and inert solids may be included in a carrier. Pharmaceutically acceptable adjuvants (buffering agents, dispersing agents) may also be incorporated into the pharmaceutical composition. Generally, compositions useful for parenteral administration of such drugs are well known; e.g. Remington's Pharmaceutical Science, 17th Ed. (Mack Publishing Company, Easton, Pa., 1990). Alternatively, compositions of the invention may be introduced into a patient's body by implantable drug delivery systems [Urquhart et al., Ann. Rev. Pharmacol. Toxicol 24:199 (1984)].

Human $LTB_4$ hydroxylase optionally is combined with or administered in concert with one or more other pharmacologic agents used to treat the conditions listed above, such as antibiotics, bronchodilators, DNA hydrolytic agents, mucolytics (e.g. n-acetyl-cysteine), actin binding or actin severing proteins (e.g., gelsolin; Matsudaira et al., Cell 54:139-140 (1988); Stossel, et al., PCT Patent Publication No. WO 94/22465, published Oct. 13, 1994; protease inhibitors; or gene therapy product (e.g., comprising the cystic fibrosis transmembrane conductance regulator (CFTR) gene); Riordan, et al., Science 245:1066-1073 (1989)).

The formulations may conveniently be presented in unit dosage form and may be prepared by any methods well known in the art of pharmacy. See, e.g., Gilman et al. (eds.)

(1990), The Pharmacological Bases of Therapeutics, 8th Ed., Pergamon Press; and Remington's Pharmaceutical Sciences, supra, Easton, Pa.; Avis et al. (eds.) (1993) Pharmaceutical Dosage Forms: Parenteral Medications Dekker, N.Y.; Lieberman et al. (eds.) (1990) Pharmaceutical Dosage Forms: Tablets Dekker, N.Y.; and Lieberman et al. (eds.) (1990), Pharmaceutical Dosage Forms: Disperse Systems Dekker, N.Y.

The enzymatic activities of leukotriene B4 hydroxylase may be enhanced in the presence of NADPH-cytochrome P-450 reductase, and/or nicotinamide adenine dinucleotide phosphate. In a preferred embodiment of the invention, leukotriene B4 hydroxylase is administered with an NADPH-cytochrome P-450 reductase and/or nicotinamide adenine dinucleotide phosphate.

This invention also provides methods for determining the presence of a nucleic acid molecule encoding human $LTB_4$ hydroxylase in test samples prepared from cells, tissues, or biological fluids, comprising contacting the test sample with isolated DNA comprising all or a portion of the nucleotide coding sequence for human $LTB_4$ hydroxylase and determining whether the isolated DNA hybridizes to a nucleic acid molecule in the test sample. DNA comprising all or a portion of the nucleotide coding sequence for human $LTB_4$ hydroxylase is also used in hybridization assays to identify and to isolate nucleic acids sharing substantial sequence identity to the coding sequence for human $LTB_4$ hydroxylase, such as nucleic acids that encode naturally-occurring allelic variants of human $LTB_4$ hydroxylase.

Also provided is a method for amplifying a nucleic acid molecule encoding human $LTB_4$ hydroxylase that is present in a test sample, comprising the use of an oligonucleotide having a portion of the nucleotide coding sequence for human $LTB_4$ hydroxylase as a primer in a polymerase chain reaction.

The following examples are offered by way of illustration only and are not intended to limit the invention in any manner. All patent and literature references cited herein are expressly incorporated.

EXAMPLE 1

Preparation and Cloning of cDNA Encoding $LTB_4$ Omega-hydroxylase cDNAs encoding human $LTB_4$ hydroxylases are synthesized by reverse transcription (RT) of human RNA and amplified by PCR. cDNA encoding the human $LTB_4$ hydroxylase CYP4F3A is prepared using total RNA from human adult leukocytes. Human adult peripheral blood neutrophils (PMNs) are separated from whole blood by fractionation on Mono-Poly resolving medium (ICN) and total RNA is prepared from the cells by the RNA STAT-60 procedure (Tel-Test Inc.). cDNAs encoding the human $LTB_4$ hydroxylases CYP4F2 and CYP4F3B are prepared using total RNA obtained from human liver. Total RNA from human adult and fetal liver (15-24 weeks) is purchased from CLONTECH. Total RNA is isolated from COS-7 cells using the RNeasy MiniKit (Qiagen).

cDNAs are generated by RT-PCR. First-strand cDNA synthesis is performed using the cDNA Cycle Kit (Invitrogen) with avian myeloblastosis virus reverse transcriptase and random primers. The cDNA is purified by phenol chloroform extraction and ethanol precipitation. PCR is performed using DNA oligonucleotide primer-pairs specific to cDNAs that encode CYP4F2 (SEQ ID NO: 1), CYP4F3A (SEQ ID NO: 3), or CYP4F3B (SEQ ID NO: 5). cDNA encoding CYP4F2 is amplified by PCR using 5'sense (SEQ ID NO: 7) and 3' anti-sense (SEQ ID NO: 8) oligonucleotides; cDNA encoding CYP4F3A is amplified by PCR using a second set of 5' sense (SEQ ID NO: 9) and 3' anti-sense (SEQ ID NO: 10) oligonucleotides, and cDNA encoding CYP4F3B is amplified by PCR using a third set of 5' sense (SEQ ID NO: 11) and 3' anti-sense (SEQ ID NO: 12) oligonucleotides. PCR is carried out at 94° C. for 1 min, 50° C. for 1 min, and 72° C. for 1.5 min; 30 cycles were followed by 1 cycle with a 10-min extension time. PCR conditions are sometimes varied with respect to time and temperature of incubation in order to optimize yield or fidelity of DNA synthesis. PCR products are analyzed on a 1 to 2% agarose gel. PCR amplified cDNAs are ligated into a suitable plasmid cloning vector, such as pCR2.1-TOPO (Invitrogen), and transformed into TOP10 bacterial cells. Plasmid DNA is purified with SNAP kits (Invitrogen). The completeness of cloned sequences encoding CYP4F2, CYP4F3A, and CYP4F3B are determined by comparing the sequences to those of SEQ ID NOs 1, 3, and 5, respectively. Sequencing is performed by automated sequencing using an ABI 3700 Capillary DNA Sequencer.

EXAMPLE 2

Expression of Human LTB4 hydroxylases CYP4F2, CYP4F3A, or CYP4F3B

Figure 2:
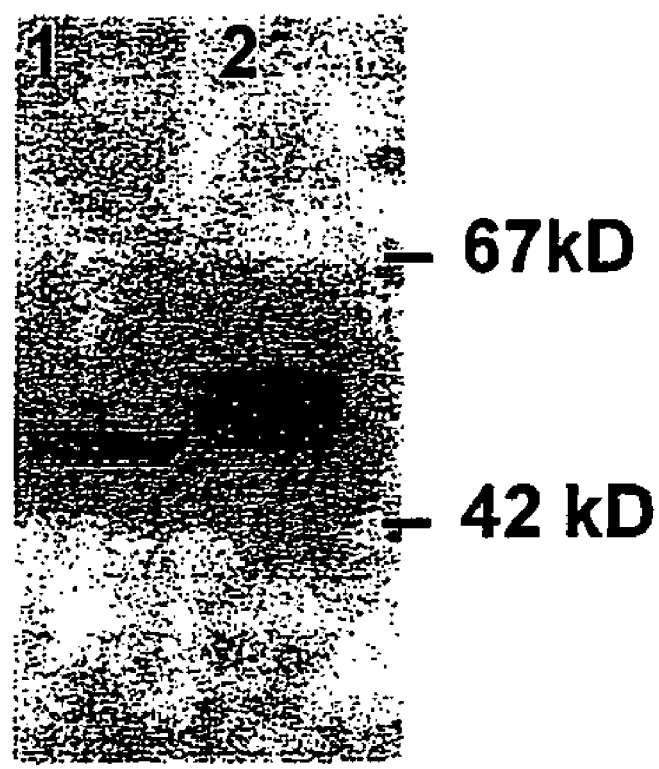
FIG. 2. The figure depicts the Western blot analysis of expression of a recombinant form of the rat LTB$_4$ hydroxylase, CYP4F5. Rat brain homogenates are known to contain LTB$_4$ hydroxylase isoforms of CYP4F. Lane 1 (control), 75 ug rat brain homogenate. Lane 2, recombinant CYP4F5 expressed in yeast.

Recombinant human $LTB_4$ hydroxylases are expressed in yeast cells. For expression in yeast, the cDNA containing the complete coding regions of CYP4F2, CYP4F3A, or CYP4F3B are re-amplified by PCR with Pfu DNA polymerase and subcloned into the yeast expression vector pYeDP60 (V60). For amplification, sense and antisense primer pairs are used that contain the sequences of SEQ ID NOs 7-12, but which also contain linker sequences at the 5' end of each oligonucleotide primer. The linker sequences contain restriction enzyme cleavage sites suitable for cloning into yeast expression vectors. The complete cDNA sequences (SEQ ID NOs 1,3, and 5) contain the translation initiation and termination signals that are necessary for protein expression in eukaryotic cells. The expression of CYP4F2, CYP4F3A, or CYP4F3B enzymes is carried out in *Saccharomyces cerevisiae* W(R), a yeast strain that has been genetically modified to over-express yeast cytochrome CYP NADPH reductase. A galactose-inducible promoter in the plasmid and in the yeast genome, respectively, is used to control recombinant gene expression. Following transformation of expression vectors containing CYP4F2, CYP4F3A, or CYP4F3B coding regions into the W(R) yeast strain by a lithium acetate method, selection of clones is carried out by growing the yeast on adenine and uracil-deficient medium. To achieve higher expression levels, the yeast cells are first grown to high density with glucose as the main energy source; thereafter, galactose is added to induce expression. Transformed yeast cells are grown to a density of ~30×10$^6$ cell/ml in SGI medium (containing per liter: casamino acids 1 g, yeast nitrogen base 7 g, glucose 20 g, tryptophan 20 mg). The cells are then diluted to ~2.5×10$^6$ cells/ml and grown for 24 h in YPGE medium (containing per liter: yeast extract 10 g, bactopeptone 10 g, glucose 5 g, ethanol 16 g). Galactose is added to a final concentration of 2% and the cells are harvested 16 h later. Yeast cell walls are disrupted with glass beads, and the microsomal fraction is obtained by differential centrifugation at +40C (20.000×g for 10 min and 100.000×g for 60 min). The microsomal pellet is homogenized in 0.05 M Tris-HCl, 20% glycerol, and 1 mM EDTA (pH 7.4) and stored at −80 C until use. The expression of a recombinant form of a mammalian $LTB_4$ hydroxylase is illustrated in FIG. 2.

EXAMPLE 3

Assay of Human $LTB_4$ Hydroxylase Activity

Yeast microsomal fractions containing oCYP4F2, CYP4F3A, or CYP4F3B (0.25-2 mg protein/ml) are incubated with 1 mM NADPH (Sigma) and 30 uM $LTB_4$ (Cayman Chemicals) in a total volume of 100 ul of 0.1 M KPHO4 (pH 7.4) buffer for 1-30 minutes at 37 C. The reactions are terminated with four volumes of ethanol and the metabolites extracted on SepPak C 18 columns. Formed metabolites are separated on a RP-HPLC Symmetry C18 (4.6×250 mm) column (Waters) by a gradient (50:50:0.1; methanol:$H_2O$:acetic acid to 100:0.1; methanol:acetic acid over 25 minutes), at 1 ml/min. Formed metabolites are monitored by an on-line UV detector at wavelength 278 nm. The retention times of formed metabolites are compared to those of authentic 20-hydroxy-$LTB_4$ (Cayman chemicals). Microsomes incubated without NADPH and control yeast microsomes with NADPH are used as controls. The identity of formed metabolites are confirmed by LC-MS analysis.

EXAMPLE 4

LC-MS Analysis of $LTB_4$ Metabolites

Formed metabolites are identified based on their masses, retention times, UV absorption properties and MS/MS spectra. $LTB_4$ metabolites are resolved by RP-HPLC. The RP-HPLC effluent is connected to an UV detector (monitoring absorption at 235 and 278 nm) and an ion trap mass spectrometer (Agilent 1100 LC/MSD trap), and is subjected to electro spray ionization. The capillary temperature is set at 350 C and the collision energy is ramped from 0.5 V to 3.0 V. Negative ions are monitored by full scan (m/z 100-400) and subjected to MS/MS (m/z 347-367->full scan).

EXAMPLE 5

Construction of a Recombinant Adenovirus Expressing a Human $LTB_4$ Hydroxylase

A cDNA containing complete CYP4F2 coding sequence is subcloned into an adenovirus shuttle plasmid pCA3 (from Microbix Biosystems; Toronto, Canada), and transfected into a suitable host strain of *E. coli*. The shuttle plasmid is linearized with a restriction enzyme that does not disrupt the ability of the recombinant CYP4F2 gene to be expressed, and is subsequently agarose gel-purified. This fragment is ligated into similarly linearized adenovirus helper dl 327 DNA, thus generating an intact viral DNA by ligation in vitro. Helper virus DNA into which the CYP4F2 gene has been ligated is subsequently transfected into the permissive host cell line HEK 293. Recombinant virus produced following transfection is plaque-purified, propagated in HEK 293 cells, and clonal stocks of recombinant virus are tested for CYP4F2 sequence by PCR using CYP4F2-specific primers. The virus clones are further purified by two rounds of subplaquing. The ability of viral recombinants to express CYP4F2 in HEK 293 cells is evaluated by Northern blotting (using oligonucleotide probes complementary to CYP4F2 cDNA sequences), and verified by Western blotting (using antibodies generated to recombinant CYP4F2 or synthetic peptides of CYP4F2 amino acid sequences). Virus clones are selected for amplification to a large-scale production of virus in HEK 293 cells, followed by purification of virions by two cycles of ultracentrifugation on cesium-chloride gradients.

EXAMPLE 6

Effect of Recombinant CYP4F on $LTB_4$-Induced Airway Hypersensitization to Methacholine in Mice To determine whether introduction of recombinant CYP4F enzyme into the airway results in reduced $LTB_4$-dependent inflammation, the inventors carried out experiments using a previously published method for inducing airway hypersensitivity (O'Byrne P M, Leikauf G D, Aizawa H, Bethel R A, Ueki I F, Holtzman M J and Nadel J A. Leukotriene B4 induces airway hyperresponsiveness in dogs. Am. J. Physiol. 1941-1946, 1985).

Figure 4:
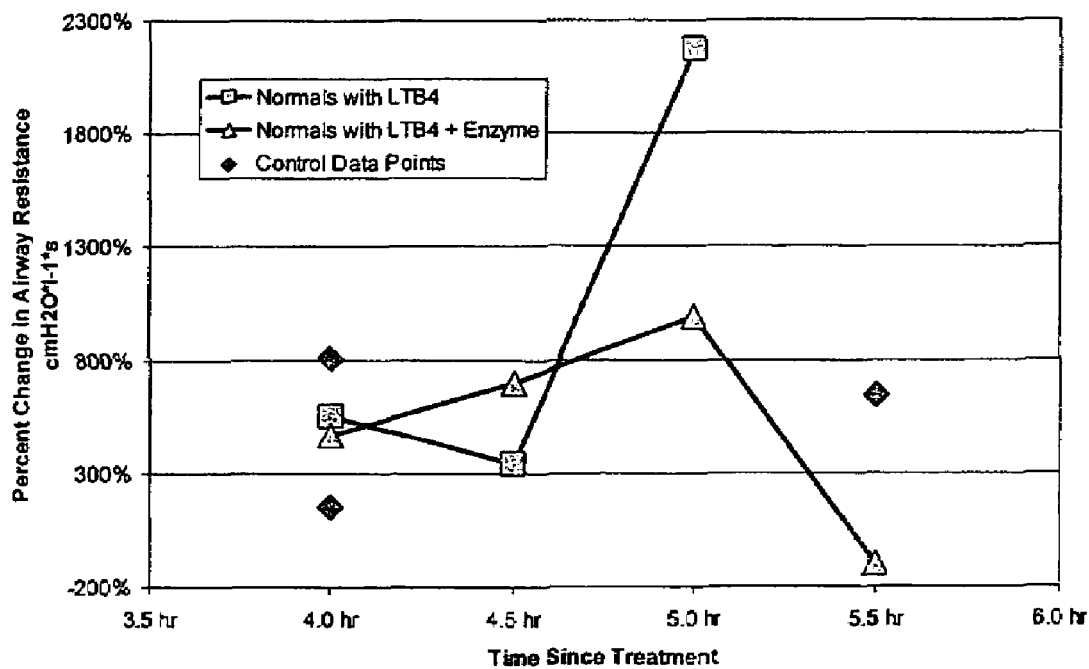
FIG. 4. The figure provides a graph summarizing the percent change in airway resistance of each animal tested in Example 6 at 1 mg dose of methacholine. Airway resistance was calculated as described in Example 6.

Groups of mice were lightly anesthetized with isoflurane, followed by intranasal delivery of one of three formulations. Group 1 received 50 microliters of saline, Group 2 received 50 microliters of saline containing $LTB_4$ (1 µg), and Group 3 received 50 microliters of saline containing $LTB_4$ (1 µg), recombinant rat LTB4 hydroxylase (CYP4F5) in a yeast microsomal extract (0.2 mg total protein), and NADPH at 1 mM concentration. The rat LTB4 hydroxylase was prepared in a yeast strain over-expressing NADPH-cytochrome P-450 reductase, as described in Examples 2; enzyme activity was assessed as described in Example 3. After anesthetizing with xylazine+ketamine (i.p.), control animals (Group 1) were intubated and placed in a plethysmograph for measurement of airway resistance. Airway resistance in response to methacholine challenge (1 mg dose) was measured at 30 seconds intervals for 180 seconds (six readings) in two of three animals from Group 1 at 4 hours after $LTB_4$ treatment and the third animal after 5.5 hours. Airway resistance was similarly measured in paired sets of animals (i.e. Group 2 and Group 3) at 4, 4.5 and 5.5 h after $LTB_4$ treatment. One animal from Group 2 died prior to the final measurement of airway resistance at 5.5 h. The table below and the graph provided as FIG. 4 summarize the percent change in airway resistance of each animal tested at the 1 mg dose of methacholine. Airway resistance was calculated by averaging the six resistance measurements at each time, subtracting the average control baseline reading from each animal from the average airway resistance obtained after methacholine challenge, dividing by the control baseline reading, and multiplying by 100 to obtain percent change.

TABLE 1

| | % Change in Airway Resistance | | |
| --- | --- | --- | --- |
| Time of Treatment | Group 1 Controls w/ Methacholate | Group 2 Normals w/LTB4 | Group 3 Normals w/LTB4 + Enzyme |
| 4.0 hr | 153% | | |
| 4.0 hr | 810% | 554% | 467% |
| 4.5 hr | | 340% | 703% |
| 5.0 hr | | 2170% | 993% |
| 5.5 hr | 648% | Animal expired | −97% |

These data suggest that a longer time of exposure to $LTB_4$ (animal 3) resulted in a large change in airway resistance in response to methacholine challenge that was greater than the highest response obtained in either of the three control animals. Interestingly, both animals that received the recombinant CYP4F enzyme in microsomal form (i.e. animal 3 and animal 4) had reduced airway resistance in response to 1 mg methacholine when compared to $LTB_4$ given alone (animal 3). Taken together, these data illustrate that delivery of recombinant CYP4F enzyme with, in this case, NADPH represents a novel therapeutic strategy to limit the pro-inflammatory effect of $LTB_4$.

Those skilled in the art will recognize, or be able to ascertain using no more then routine experimentation, numerous equivalents to the specific subject matter described herein. Such equivalents are considered to be within the scope of this invention and encompassed by the following claims.

What is claimed is:

1. A method of treating a human or non-human animal suffering from a respiratory disease by reducing the amount of leukotriene $B_4$ in a respiratory system of the human or non-human animal comprising the step of administering an effective amount of leukotriene $B_4$ hydroxylase to the human or non-human animal in need of such treatment.

2. The method of claim 1 wherein said leukotriene $B_4$ hydroxylase is administered in combination with nicotinamide adenine dinucleotide phosphate.

3. The method of claim 1 wherein said leukotriene $B_4$ hydroxylase is administered in combination with an NADPH-cytochrome P-450 reductase.

4. The method of claim 1 wherein said leukotriene $B_4$ hydroxylase is administered in combination with nicotinamide adenine dinucleotide phosphate and an NADPH-cytochrome P-450 reductase.

5. A method of reducing inflammation in a respiratory system of a human or non-human animal by reducing the amount of leukotriene $B_4$ in the human or non-human animal's respiratory system comprising the step of administering an effective amount of leukotriene $B_4$ hydroxylase to the human or non-human animal in need of such treatment.

6. The method of claim 5 wherein said leukotriene $B_4$ hydroxylase is administered in combination with nicotinamide adenine dinucleotide phosphate.

7. The method of claim 5 wherein said leukotriene $B_4$ hydroxylase is administered in combination with an NADPH-cytochrome P-450 reductase.

8. The method of claim 5 wherein said leukotriene $B_4$ hydroxylase is administered in combination with nicotinamide adenine dinucleotide phosphate and an NADPH-cytochrome P-450 reductase.

9. A method of alleviating symptoms of respiratory disease in a human or non-human animal comprising the step of administering an effective amount of leukotriene $B_4$ hydroxylase to the human or non-human animal in need of such treatment.

10. The method of claim 9 wherein said leukotriene $B_4$ hydroxylase is administered in combination with nicotinamide adenine dinucleotide phosphate.

11. The method of claim 9 wherein said leukotriene $B_4$ hydroxylase is administered in combination with an NADPH-cytochrome P-450 reductase.

12. The method of claim 9 wherein said leukotriene $B_4$ hydroxylase is administered in combination with nicotinamide adenine dinucleotide phosphate and an NADPH-cytochrome P450 reductase.

13. The method of claim 9 wherein the respiratory disease is asthma, infectious pneumonia, bronchitis, tracheobronchitis, bronchiectasis, cystic fibrosis, tuberculosis, hay fever or fungal infection.

* * * * *